United States Patent [19]

Polson

[11] Patent Number: 4,550,019
[45] Date of Patent: Oct. 29, 1985

[54] MANUFACTURE AND USE OF FOWL EGG ANTIBODIES

[75] Inventor: Alfred Polson, Camps Bay, South Africa

[73] Assignee: South Africa Inventions Development Corporation, Pretoria, South Africa

[21] Appl. No.: 399,094

[22] Filed: Jul. 16, 1982

Related U.S. Application Data

[63] Continuation-in-part of Ser. No. 20,786, Mar. 15, 1979, Pat. No. 4,357,272.

[51] Int. Cl.$^4$ .................... A61K 39/42; A61K 39/40; A61K 39/12; A61K 39/00
[52] U.S. Cl. ........................................ 424/85; 424/86; 424/87; 424/88; 424/89; 514/6; 260/112 B; 260/112 R; 435/7; 435/810; 436/547; 436/539; 436/817; 436/823
[58] Field of Search ...................... 260/112 R, 112 B; 424/85, 88, 95, 105, 86, 87; 435/7, 810; 436/517, 519, 532, 542, 544, 545, 546, 547

[56] References Cited

U.S. PATENT DOCUMENTS

| | | | |
|---|---|---|---|
| 2,543,215 | 2/1951 | Williams et al. | 260/112 B |
| 4,021,534 | 5/1977 | Lafontaine | 424/1 |
| 4,165,370 | 8/1979 | Coval | 424/86 |
| 4,357,272 | 11/1982 | Polson | 260/112 R |

OTHER PUBLICATIONS

Heller et al., *Res. Vet. Sci.* V 18, pp. 117–120 1975 "The Immune Response of Hens to Multiple *E. Coli* Injections and Transfer of Immunoglobulins to the Egg and Hatched Chick".

Stedman *J. of Comp. Pathology,* V. 79, No. 4, 1969 pp. 507–516.

Yamamoto *Japan J. Vet. Res.,* V. 23 No. 4, 1975 pp. 131–140.

Williams *Methods in Immunology & Immunochemistry,* Academic Press, NY, V. 1 1967, pp. 209–212, 229–237, 244–255.

*Primary Examiner*—Thomas G. Wiseman
*Assistant Examiner*—Robin Lyn Teskin
*Attorney, Agent, or Firm*—Millen & White

[57] ABSTRACT

Immunological preparations are prepared by immunizing hens with an immunogen having a molecular or particle weight of at least 30,000, to a stage of hyperimmunization at which there occurs a plateau-like levelling-off of the antibody content of the serum. The immunogenicity of the immunogen can be enhanced by enlarging the immunogen particle mass. The eggs of the immunized hens are collected, the yolk is separated from the eggs, followed by separation of the lipid content of the yolk. The antibodies in the egg yolk are then rendered indispersable with the aid of a water-soluble linear filamentary non-charged polymer precipitant such as PEG and the indispersable antibodies are recovered. This precipitation of antibodies is advantageously preceded by a precipitation of caseinaceous proteins, lipid and yolk particles at lower polymer concentrations. Selected antibodies (IgY or IgG) can be concentrated by pH-controlled fractional precipitation with PEG. The immunological preparations are useful for micro-assays and in appropriate cases also for the treatment or prophylaxis of pathological conditions.

59 Claims, No Drawings

MANUFACTURE AND USE OF FOWL EGG ANTIBODIES

This is a continuation-in-part to Ser. No. 020,786 filed Mar. 15, 1979, recently allowed U.S. Pat. No. 4,357,272.

BACKGROUND OF THE INVENTION

1. Related Applications

The present invention contains subject matter useful in connection with the teachings of copending U.S. application Ser. Nos. 392,111 now allowed U.S. Pat. No. 4,478,946 and 399,093 claiming the priority of South African application Nos. 81/4481 and 81/4898 respectively of which the present applicant is a coapplicant. By the same token the present application discloses certain preferred embodiments which can be combined with advantage with teachings of the said copending applications.

The present invention relates to immunological preparations, their manufacture and use.

2. The Prior Art

It is known that birds, e.g. laying hens, transfer their immunity to the yolk of their eggs and thereby to their offspring (F. W. Rogers Brambell "The transmission of passive immunity from mother to young" (1970) North Holland Publishing Company, Amsterdam, London).

The present invention is based on the development of novel or improved techniques for putting this phenomenon to practical use, thereby to achieve a number of novel results and advantages.

The invention deals with a number of aspects each requiring a separate consideration of the relevant prior art:

(1) the eliciting of antibodies in fowl eggs and the cropping of the eggs for purposes of antibody recovery (2) the recovery and purification of the antibodies from fowl eggs;

(3) novel uses of antibodies recovered from fowl eggs.

In Williams, Methods in Immunology and Immunochemistry, Ace Press NY, vol. 1, 1967 pages 209-212, 229, 337, 224-245 there is described inter alia the active immunisation of fowls, male and female, against a variety of immunogens and the recovery of antibodies from the fowl serum. However, there is no disclosure of the transfer of antibodies to the eggs of hens where such antibodies have been elicited against immunogens which are non-pathogenic in hens.

Aulesio et alia, PSEBM (1969) 131, 1150-1153 describe immunising fowl hens against microbes which are pathogenic in fowls and the resulting antibody levels were determined both in the hen serum and the egg yolk. The purpose of this work was the development of methods for monitoring chicken flocks for evidence of exposure to microbal infections. No suggestion is made to put the antibodies themselves to any practical use, nor is any method disclosed which could be put to practical use for the commercial manufacture of egg yolk antibodies. Quite clearly, the immunisation regimens employed had not yet led to optimised antibody levels in the yolk. The results strongly suggest a connection between pathogenicity of the immunogens and immunoresponse. It is stated that subsequent actual infection with pathogens (by injection of living rickettsiae) resulted in a manifold further rise of the antibody titre.

Stedman et alia. J Comp. Path., 79 (1969) 507-516) describe the recovery of anti-Newcastle disease antibodies from the egg yolk of hens which had suffered natural exposure to Newcastle disease and which had recovered from the disease. Again, the antibody levels had not reached optimum levels, because it is suggested that hyperimmunisation of the hens would have resulted in increased titres. However, no hyperimmunisation regimen is disclosed, nor an interrelationship between a hyperimmunisation regimen and an egg cropping regimen for purposes of achieving satisfactory yields of homogeneous antibodies from egg yolk. In the conclusion egg yolks are mentioned as a possible source for specific antibodies. However, no method for achieving this is disclosed and the suggestion is qualified by doubts as to the susceptibility of hens against antigens other than Newcastle disease. The recovery method for isolating or concentrating antibodies from the egg yolk results in substantial damage to the antibodies and in substantial losses. The damage is manifested in an "inherent instability of the immunoglobulins" and in substantial aggregation, the dimer content alone amounting to about 20%. Moreover, the fractionation and purification procedure involves a sequence of 8 steps (or more if the repetition of certain steps is counted as separate steps). The procedure has to be carried out at very low temperature and takes more than two days to complete.

Goudswaard et alia, Poultry Sci. vol. 56, no. 6 (November 1977), 1847-1841 describe the recovery of naturally occurring antibodies from egg white and egg yolk. The differences between fowl and mammalian antibodies are clearly not recognised. The antibodies here being dealt with are those which occur in the fowl due to natural exposure to disease. The purification method (as in Stedman et alia, see above) uses for defatting a surfactant, namely dextran sulphate—which in contrast to ordinary dextran is a potent ionic surfactant, followed by dialysis, salting out and chromatography on Sephadex and/or DEAE cellulose. Again the methods are such that they result in substantial damage to the egg antibodies.

Yamamoto et alia, Jap. J. vet. res., 23, 131-140 (1975) describe the immunisation of hens against sheep red cells by intravenous injection three times daily followed immediately by egg collection up to the 28th day from the beginning of the immunisation. Between the 10th and the 19th day of this regimen the egg yolk was found to contain small amounts of antibodies, mostly IgM (a macro-globulin which is undesirable for use in most immuno assays) and very little IgG. As from the 25th day the antibody level had dropped to negligible levels. This reference clearly contains no teaching which would encourage the use of egg yolk as a commercial source of antibodies and in fact the methods there disclosed are unsuitable for that purpose. Moreover, the minute quantities of IgG antibodies which appear in the egg yolk for a few days only, following the immunisation regimen disclosed in the reference, whilst being of scientific interest, have inferior properties for most practical purposes. The method employed for recovering and purifying the antibodies involves separating the yolk, high speed centrifugation and salting out with ammonium sulphate, i.e. methods similar to the aforementioned prior art. This recovery method, as is the case for all the prior art methods referred to above, results in substantial damage to and losses of the desired fowl egg antibodies. The extent of this damage and of these losses, as well as the avoidability thereof had not been known or appreciated according to the prior art.

The prior art did not appreciate and make allowance for the fact that there exist substantial differences between the gamma-globulins which occur in the egg yolk of fowl eggs on the one hand and mammalic (including human) gammaglobulins on the other hand. Accordingly it was not realised that due to those differences the aforementioned prior art procedures which had been applied successfully to the purification of mammalic antibodies are unsuitable for the recovery without substantial losses of undamaged, stable and non-aggregated gammaglobulins from egg yolk.

Firstly the source materials from which the gammaglobulins are recovered are substantially different. Conventional mammalic immunoglobulin preparations have mostly been recovered from blood serum. This is obtained from whole blood after removal of fibrinogen by clotting. The serum is a clear liquid containing about 6.5 to 7% by volume of dissolved proteins represented by about 0.8 to 1% gammaglobulin, 3.5% albumin, 2.5% miscellaneous proteins (including glyco-proteins, beta-lipo-proteins, IgG, ferritin, prealbumin I and II. There is no caseinaceous matter in mammalic serum and little or no free lipid matter. By way of contrast, egg yolk contains about 25% by volume yolk granules. A further approximately 25% by volume is composed of about equal parts, i.e., about 10 to 15% by volume each of caseinaceous proteins and free lipids. The remaining 50% by volume contain 5% proteins in aqueous solution (sometimes referred to as "alpha-, beta- and gamma-vitellines"). These are represented by about 2.5 to 3.6% gammaglobulin, 2.5 to 1.4% betaglobulin (in about equal parts, besides other minor contaminants. The albumins and beta-globulins of egg yolk are different from the albumins and beta-globulins in mammalian blood.

Secondly, and perhaps most important of all, the immunoglobulins themselves in egg yolk are chemically and physically significantly different from immunoglobulins in human or other mammalian serum. These differences, some of which were only discovered in the course of making the present invention, are inter alia the following:

(i) different amino acid compositions and sequences in the basic molecules, (ii) different electrophoretic mobilities (IgY has much higher mobility than the corresponding mammalian serum IgG)

(iii) materially different isoelectric pH values, namely about 5.8 in the case of egg yolk gammaglobulin and about 6.8 in the case of mammalian serum IgG. This in turn is evidence of material difference in the ratios of carboxyl and amino groups (egg yolk gammaglobulin having relatively more of the former).

(iv) Different molecular weights, namely 175000 daltons in the case of egg yolk gammaglobulins as compared with 150000 daltons for mammalian IgG.

(v) Substantially different chemical stabilities, for which reason as stated above egg yolk gammaglobulins suffer severe damage when subjected to the conditions of most conventional purification processes which have been used successfully for IgG from mammals. Egg yolk gammaglobulin requires the presence of non-ionic surfactants as stabilisers in certain conditions where mammalian IgG is stable without such surfactant.

(vi) Ionic detergents inhibit the antigen-antibody reaction of mammalic IgG, but do not (at least not at modest concentrations) have an effect on the antibody-antigen reaction of egg yolk gammaglobulin.

(vii) Mammalic IgG remains in the monomeric form in low and high molar salt solution. IgY is monomeric in 0.15 molar NaCl and is dimeric in 1.5M NaCl.

U.S. Pat. No. 3,415,304 describes and claims inter alia processes for concentrating and purifying mammalian gammaglobulins from blood serum using water-soluble, linear, filamentary, non-charged polymers such as polyethylene glycol as a precipitant and fractionating agent. Since then a considerable number of modifications for special practical applications of that process have been published. However, in the field of isolating or purifying mammalian immunoglobulins these fractionating or purification processes have only been one type out of a large number of alternative available types, e.g. cryoethanol fractionation, precipitation with chloroform or other solvents or various salting out procedures, e.g. with ammonium sulphate. Moreover the polyalkyleneglycol methods for purifying mammalian serum gammaglobulins were designed to be applied to gammaglobulin concentrates which had already been subjected to substantial prepurification, and none of these concentrates, let alone their source materials, are at all similar in composition to fowl egg yolk.

To date no method has existed suitable for fractionating gammaglobulins of a given class (e.g. mammalian serum gammaglobulins or fowl egg yolk gammaglobulins) on a commercial scale for the purpose of concentrating or purifying antibodies with a specificity against particular antigens from antibodies against other antigens.

Immunological preparations comprising antibodies can be put to a variety of uses, including the passive immunisation of animals (including humans) and to an ever increasing extent, as immuno regants for immunosorbtive processes and in particular for quantitative and qualitative analytical tests, in particular micro assays for diagnostic, pathological, forensic and pharmacokinetic investigations.

In the therapeutic field there is a need for greater variety and specificity and improved hypo-alergenicity, bearing in mind that conventional preparations based on mammalic sera are inclined to lead to allergic reactions including anaphylactic shock.

The conventional methods of producing passive immunising preparations against specific conditions, e.g. anti-tetanus preparations, anti-venines and anti-toxins involve the immunisation of mammals such as horses, sheep, goats and the bleeding of such animals for the recovery of the antibodies from the blood. Similar procedures, sometimes also involving smaller mammals such as rabbits or guinea pigs are employed in the production of antibodies for diagnostic and similar microanalytical testing procedures. The amounts of immunogen required for immunising a single animal are comparatively large. The immunising period is comparatively long and the bleeding of the animals is traumatic for the animals, eventually affects the health of the animals and is unpleasant for the person(s) having to recover the blood besides being often quite difficult and involving specialised skills.

It is quite generally an object of the invention to provide improvements in the aforegoing regard.

It is an object of the invention to provide fowl eggs as a practical and convenient source of a wide variety of antibodies, more particularly antibodies of a character novel per se.

It is a further object of the invention to improve the economics of antibody production by the prolonged recovery of antibody bearing eggs during the course of the laying periods of hens.

It is a further object to produce useful or increased yields of antibodies and antibodies of improved quality, elicited by immunogenic determinants, including those which in the past had modest to poor immunogenic effectiveness of hens, in particular from haptens and immunogenic determinant-bearing molecules of relatively low molecular weight, but which nevertheless produce a satisfactory immunoresponse in mammals.

It is an object to provide a method by which new antibodies or specific antibodies can be produced at short notice in a comparatively short period of time, namely a shorter period of time than with most laboratory animals conventionally used for the purpose, to provide at relatively low cost either small amounts of antibodies for specialised purposes or larger amounts and if desired continuous supplies of such antibodies over prolonged periods with minimum distress and discomfort to test animals. It is a further object to provide antibodies of particularly high selectivity and avidity.

It is a further object to provide a method suitable for eliciting antibodies in relatively large amounts, even when only very small amounts of immunogenic determinant material are available.

It is yet a further object to produce egg yolk antibodies of high homogeneity, high purity, freedom from proteolytic enzymes, high stability, being substantially undamaged and free of dimers or higher aggregates.

Further objects, advantages and uses of the invention will become apparent from what follows.

DESCRIPTION OF THE INVENTION

In the present specification I use the term "immunogenic determinant" to denote a substance, molecule or part of a molecule which when present in an immunogen is responsible for a specific immune response when the immunogen acts upon an immune system, i.e. living antibody-producing cells. By "immune response" I mean that antibodies are formed by the immune system in response to an immunogenic stimulus elicited by the immunogen. The antibodies will include antibodies more or less specific to the immunogenic determinants (or combination thereof) of the immunogen.

The term "immunogen" is used for a substance which elicits the formation of antibodies as aforesaid. The term "antigen" denotes a substance which couples with a matching antibody, thereby being bound and "neutralised" by the latter. In practice "antigens" and "immunogens" in a given context are often the same substances, for which reason the two terms are frequently used as synonyms, also on occasion in the present specification.

A hapten denotes a usually small immunogenic determinant which only becomes an immunogen when coupled to a sufficiently large carrier for a given immunosystem. In certain instances an antigen may be able to couple with a given antibody yet may be too small to itself elicit the formation of such antibody in a given immune system In that case, although the "antigen" possesses "immunogenic determinants" (or for that matter "antigenic determinants") specific to the antibody in question, such antigen is not an "immunogen" for the given immune system, but a hapten.

In prior art literature the gammaglobulins in egg yolk have been referred to as IgY. As in the case of mammalic gammaglobulins, because the significant differences between these classes of antibodies of mammalic and avian origin respectively were not recognised. In the present specification these avian gammaglobulins, which according to the invention are to be recovered from fowl egg yolk, are referred to as IgY.

When the immune system of an animal is challenged with an immunogen (e.g. by injection) to produce antibodies against an antigen having antigenic determinants corresponding to the immunogenic determinants of the immunogen, that is known as active immunisation; whilst the administration to an animal, e.g. by injection of antibodies extraneously produced, e.g. in a different animal in order to produce resistance against antigens for which the antibodies are specific, is known as passive immunisation.

According to one aspect of the present invention, there is provided a process for preparing an immunlogical preparation consisting of or comprising IgY antibodies, which comprises actively immunising hens against a given antigen, collecting eggs of the hens thus immunised and containing antibodies against such antigen and separating the antibodies from the yolk of the eggs. In accordance with preferred embodiments of the invention, this is achieved by separating off the lipid content of the egg yolk, rendering the antibodies in the egg yolk indispersable by mixing the egg yolk with a water-soluble linear filamentary non-charged polymer precipitant and recovering the indispersable antibodies separated from the resulting supernatant.

According to the aforesaid prior art, e.g. relating to the scientific determination and study of antibodies in the eggs of immunised hens, the immunisation was not truly optimised, in fact it was often very far removed from the optimum, and the antibodies were determined in eggs usually recovered during the period following shortly after the immunisation period and often shortly after the beginning of the immunisation. Also, the immunogens used for immunising were often not suitable for eliciting a strong immune response in the hens.

Therefore the present invention teaches actively immunising a fowl hen by injection with an immunogen carrying immunogenic determinants specific to elicit the desired IgY antibodies, wherein the immunogen is selected with such molecular or particle weight being not less than 30,000 daltons, preferably not less than 100000 daltons and more preferably having a molecular or particle weight greater than 150000 daltons, and carries the determinant in such number and so exposed on the immunogen that an immune response is elicited in the fowl which produces substantial antibody concentrations in the eggs.

It has been found in accordance with the present invention, that substances carrying the required immunogenic determinants (and which would be satisfactory immunogens in mammals), but being of comparatively low molecular weight, e.g. less than 100000 daltons and particularly less than 30000 daltons, have a comparatively low or even negligible immunogenicity in fowl hens for purposes of producing the desired IgY antibodies in the hen and transferred to the egg and egg yolk as compared with high molecular weight immunogens of molecular weight greater than 150000. A preferred feature of the invention provides that the immunogenic properties of comparatively low molecular weight substances carrying the required immunogenic determinants are enhanced by the particle weight of a molecule carrying the desired immunogenic determinants being increased to a level suitable for the required immune response in the fowl, namely by attaching the molecules to a carrier substance, the hen then being immunised with the molecules thus attached. According to some embodiments the molecules are attached to molecules of the same kind serving as carrier substances thus forming an aggregate. Such aggregation may for example be achieved by covalent reaction with a cross-linking reagent, e.g. with glutaraldehyde, in particular in the case of molecules carrying basic groups such as amino groups or with carbodiimines. e.g. for cross-linking carboxyl groups on the molecules. The molecules may also be attached by covalent bonding reaction to a different carrier substance, e.g. to carrier molecules of a different kind. Once again a cross-linking reagent as aforesaid may be used.

The molecules carrying the immunogenic determinants may be attached with particular advantage to the exterior surface of bacterial particles serving as carrier substance. For example they may be attached to the exterior surface of "naked" bacteria particles by adsorption. Naked bacteria particles are bacteria particles which have been stripped of their natural immunogenic determinants by suitable chemical reaction. In many bacteria, e.g. gram negative bacteria such as Salmonella, this natural immunogenic zone, constituting the immunogenic determinants of the bacteria is largely or wholly confined to an outer layer containing the O-antigens, i.e. the O-specific long-chain poly-saccharide immunogenic (antigenic)determinant, covalently bonded to a lipophylic, antigenically substantially inert surface of the cell wall of the bacterial particle. It was known that this antigenic determinant zone can be stripped off, e.g. by acid hydrolysis, resulting in "naked bacteria" which have substantially or wholly lost their natural characteristic immunogenicity. (C. Galanos, O. Luderitz and O. Westphal; Eur. J.Bio.chem. 24 (1971), 116–122).

In appropriate cases the molecules carrying the desired immunogenic determinants may be attached to the exterior surface of such "naked" bacteria particles by adsorption, in particular if the molecules carry a lipophylic region suitable for such adsorption. Of course, it is important that the desired immunogenic determinants are not mainly associated with such lipophylic region, because in that event they may become screened off following such adsorption thus being not available for the immune response. Also, care must be taken that the adsorbed molecules do not become desorbed, e.g. due to their being administered to the fowl in the form of an oily emulsion.

More preferred is the use as the immunogen of molecules carrying the immunogenic determinants covalently bonded to the exterior surface of the naked bacteria particles. Such immunogens may be produced, as will be exemplified further below by a process forming the subject of a copending application claiming the priority of RSA patent application 81/4898, which by reference thereto is to be considered as a part of the present disclosure.

The covalent bonding of a molecule carrying the desired immunogenic determinants to a carrier molecule or carrier particle is preferably conducted with the aid of one or more bifunctional linking reagents having two functional groups of which at least one is covalently reactive to enter into a bonding reaction with a reactive site of the bacterial particle whilst at least one other functional group is reactive to enter into a bonding reaction with a reactive site of the immunogenic determinant or a molecule carrying the determinant.

The at least two functional groups of the linking reagent may be identical or different. If they are different, the one group may be specifically selected to react with a specific type of reactive site on the carrier particle, whilst the other may be specifically selected to react with a specific type of reactive site on the immunogenic determinants. Many immunogenic determinants are likely to have several types of reactive sites, of which some are likely to be more involved than others in the peculiar and specific immunogenic activity of such determinant, i.e. more specifically involved in eliciting an immune response specific to that determinant. For that reason the choice of type of site most suitable for bonding the immunogenic determinant to the bacterial particle, whilst preserving a maximum of specific immunogenic activity of the determinant should be made with due regard to this principle, if necessary by simple experiment with different linking reagents.

Typical functional groups of linking reagents are

| Functional groups | Reacts with |
|---|---|
| Aldehyde | primary amines |
| Imide | primary amines |
| Amino | aldehyde |
| Cyano | hydroxyl groups |
| Halogen (e.g. bromine) | thiol groups |
| Carboxyl groups | primary amines |
| Activated carboxyl groups (e.g. N—Succinimidyl esters of carboxylic acids)* | primary amines or hydroxyl groups |
| Anhydrides (e.g. Succinic anhydride and maleic anhydride) | primary amines |
| Maleimide derivatives | thiol groups |

*e.g. N—hydroxy succinimide ester of N—(-4-carboxycyclohexyl methyl)maleimide.

Preferred examples of such linking reagents are:

Dialdehydes, in particular aliphatic dialdehydes, preferably glutaraldehyde and its higher homologues having from 4 to 20 carbon atoms; separating the aldehyde groups;

Diamines, more particularly compounds wherein the amino groups are separated by from 2, preferably 4, to 20 carbon atoms, e.g. hexamethylenediamine;

Cyanogen bromide. It reacts in the first step with the —OH groups of the sugar residues of the polysaccharide cell wall components to form activated imidoesters which in turn react in the second step with the amino groups of the antigens.

Further preferred linking compounds are described in the specific examples.

The aforesaid linking reagents may be caused to react with the respective reactive sites in manners known per se, more particularly as set out in the aforegoing table.

In preferred embodiments of the process, the linking reagent is first reacted with one of the two partners to be grafted together to form a reactive intermediate which is then reacted with the other partner. The first said partner may be either the immunogenic determinant or the carrier.

Alternatively, both partners may each be reacted (e.g. separately) with a linking compound to form reactive intermediates which intermediates in turn are then reactively bonded together.

In order to avoid undesirable cross-linking of either the immunogenic determinant or the carrier, it will be advantageous to employ a linking compound having two different functional groups, one group being selective for the reactive sites of the immunogenic determinants and the other being selective for the reactive sites of the carrier. If either the determinant or the carrier molecule or particle lack a reactive group suitable for the covalent bonding reaction with the bifunctional linking compound, a reactive derivative is formed by introducing such reactive group by an appropriate reaction, e.g. with a different bifunctional linking compound. The same applies if it is considered undesirable to sacrifice any of the existing reactive groups of the antigen for the bonding reaction, because their preservation is considered important for a desired immune response.

It is preferred for reasons of geometry and improved immune response to select a linking compound or compounds adapted to provide a relatively long linking chain, e.g. an aliphatic carbon chain of preferably at least 3, up to about 20, more preferably from 4 to 10 carbon atoms between the immunogenic determinant and the carrier.

The above described techniques improve the immune response of the hens to otherwise weak immunogens and permit such response to be elicited where otherwise there would have been no noticeable response at all. However, these techniques can even be used to improve the rate of antibody formation and antibody yields to be attained from the eggs of the hen in cases where the immunogen used for the active immunisation is relatively large and quite capable as such to elicit the desired immune response. This was observed for example when immunising hens against mammalic gammaglobulins which are relatively large immunogens (approximately 150000 daltons).

However, the improvement manifests itself not only in the rate of the response and the yield of IgY antibodies, but also in the quality of the antibodies, namely in their avidity (i.e. their ability to bind antigens in terms of strength and capacity of binding), their specificity, stability and uniformity.

However, the aforesaid factors are also, according to the teachings of the present invention, greatly influenced by the intensity and duration of the immunisation and the timing of the collection of the eggs for IgY recovery in relation to the immunisation regimen. If an immunogen is used which elicits a reasonable immune reponse in the hen, it will be found that antibodies against the immunogen are to be found in the eggs of the hen within days of the commencement of the immunisation, or at the latest shortly after the first repeat immunisation. However, at this early stage of the immune response the antibodies occurring in the egg, particularly in the egg white, but to some extent also in the egg yolk, comprise a considerable proportion of macro-globulins (IgM) which are inclined to interfere with some sensitive micro analytical test based on antigen-antibody reactions. However, these IgM antibodies can be used for some passive immunisation purposes. Similarly, the gammaglobulins which occur in the eggs at this early phase of the immunisation regimen are of inferior quality as regards stability, uniformity and avidity. Nevertheless these antibodies can be put to practical use if necessary, both for passive immunisation as well as for some micro-analytical purpose in cases of urgent need, e.g. if insufficient time is available for any reason whatsoever to await the formation of superior antibodies as described further below.

However, in the great majority of embodiments of the present invention it is greatly preferred for the active immunisation of the hen against the determinants of the immunogen to be carried out repeatedly over a period of several weeks and usually not less than 3 weeks thereby to raise the immune response in progressive steps over that period until the antibody level in the serum of the hen has reached at least that stage of hyperimmunisation which is indicated by a plateau-like levelling-off and persistence of the concentration of antibodies against the determinants in the serum of the fowl. Once that stage has been reached, it is found that high antibody concentrations (often higher than in the serum) can be recovered persistently over a long period from the egg yolk, e.g. from eggs collected over periods of months and even the entire laying period of the hen.

The period of time after which that stage of hyperimmunisation is reached depends not only on the immunisation regimen itself, i.e. the frequency and dosages of the immunisations and on the immunogenicity of the immunogen, but also on the breed of hen and even the particular strain. However, the latter differences and individual differences from one hen to another usually largely disappear after prolonged immunisation. Suitable immunisation regimens involve weekly and more preferably twice weekly immunisations for between two and four weeks, preferably three weeks, followed by one or more immunisations at weekly intervals, e.g. at least one such further immunisation. From then on the antibody level may persist plateau-like over prolonged periods. The term "plateau-like levelling-of" does not necessarily mean a complete constancy. In some cases the antibody level in the eggs may gradually decline over a prolonged period.

In other cases it may even increase further, but at a decreased rate. Persistently high and preferably even increasing antibody levels are enhanced by the administration to the hen of booster injections from time to time, e.g. at monthly intervals. In that manner it is possible to recover large amounts of antibodies from a single hen not only for the duration of a full laying period, but for the entire productive life of the hen, using surprisingly small quantities of immunogen and with negligible discomfort caused to the hen.

In contrast to some of the aforesaid prior art where the antibodies of interest disappeared within about 3 weeks from the start of the immunisation, the present invention thus permits continued cropping of eggs for antibody recovery from a given hen over a period of months and even years. Moreover, the IgY which is recovered from eggs collected once the aforesaid plateau-like levelling-off has been attained is of different character and quality compared with gammaglobulins recoverable during the early phase of the immunisation. These IgY antibodies have improved stability, substantially improved avidity and substantially improved uniformity. In some cases there is an improvement by orders of magnitude over comparable prior art products. For that reason these antibodies are to be considered novel products per se, quite apart from the fact that the present invention provides novel antibodies and antibody preparations quite different from any such antibodies or preparations produced previously.

The products according to the invention also acquire novel properties as a result of the novel separation, concentration and purification procedures provided by the present invention which in contrast to prior art procedures do not damage the IgY antibodies. Thus, according to a further aspect of the invention, the process according to the invention includes a purification or concentration step for the IgY which comprises forming a 2-phase aqueous system, a first phase of this system containing antibodies to be purified or concentrated and a second phase of the system containing dispersed therein a water-soluble, linear, filamentary, non-charged polymer in a concentration sufficiently high to substantially suppress the solubility or dispersibility of such antibodies and transferring impurities from the first phase to the second phase for removal in the latter.

The step involving the 2-phase aqueous system is preferably preceded by a step of rendering indispersable and separating yolk constituents other than antibodies while maintaining the antibodies in solution or dispersion. This step may similarly be carried out using a water-soluble linear filamentary non-charged polymer as a precipitate in a concentration less than that at which substantial precipitation of the antibodies takes place.

According to a preferred embodiment of the aforementioned 2-phase process, the first phase contains substantially all the IgY antibodies of the system and the second phase is substantially devoid of antibodies.

More particularly the step involving the two phase aqueous system comprises introducing into an aqueous dispersion of the antibodies the polymer to a concentration sufficient to selectively substantially suppress the dispersibility of the antibodies and separating purified antibodies thus rendered indispersible from an aqueous phase containing dissolved therein the polymer. Preferably the concentration of the polymer corresponds in precipitating power to a concentration of polyethyleneglycol (PEG) 6000 higher than 11% and lower than 14% by weight per volume of aqueous yolk material.

A criterion in selecting the precipitant (polymer) is that the amount required of "precipitant" for rendering indispersable, must not increase the viscosity of the aqueous medium comprising the egg yolk at the prevailing temperature to a level where it becomes unduly difficult to carry out the process.

Suitable "precipitants" are in particular selected from polyalkylene glycols, for example polyethylene glycol, polypropylene glycol or mixed polymers of ethylene glycol and higher homologues such as propylene glycol or poly-1,4-dihydroxy butaneglycol. Dextran may also be used advantageously. Preferably, in all cases the molecular weight of the precipitant is within the range 2,000 to 30,000 daltons.

Examples of other linear filamentary non-charged polymers which, as confirmed by various experiments, can be used but are less preferred at present are nonylphenolethoxylate, polyvinyl alcohol and polyvinyl pyrrolidene.

Because of its ready commercial availability and advantageous properties it is preferred to use polyethylene glycol (PEG) more particular of molecular weight between 2,000 and 30,000, preferably of molecular weight between 4,000 to 9,000, say substantially 6,000. For that reason PEG 6,000 will be stressed in the following.

When using a precipitant other than PEG of M.wt. 6,000 the required amount, equivalent to a known required amount of PEG 6,000, may be calculated in most cases at least approximately from the formula $$\beta = \frac{\overline{V}}{2,303}\left(1 + \frac{r_s}{r_r}\right)^3$$

in which $\beta$ is inversely proportional to the concentration required;
$\overline{V}$ = partial specific volume of the polymer;
$r_r$ = radius of the polymer molecule;
$r_s$ = radius or stokes radius of the particle to be precipitated.

The theory underlying the above formula is discussed more fully in Biochem et Biophys.Acta. 229 (1971) 535–546.

On inspection of the equation, it would be clear that if $r_r$ be small, $\beta$ the slope of the precipitation curve would be greater, consequently complete separation would occur over a narrow range. This occurs with synthetic organic polymers. When $r_r$ is large, as with dextran, the slope ($\beta$) of the precipitation curve would be less and complete precipitation will occur over a wider range of dextran concentrations. As the excluded volume (which is a function of total length of the polymer molecules) of a thinner polymer is greater than that of a thicker polymer it stands to reason that the thin polymer will produce precipitation of the substance at a lower weight concentration than the polymer of greater diameter would do.

The relationship between required concentration and molecular weight of the precipitant is substantially linear in practice for most cases.

The term "precipitation" and to "precipitate" as used in the present specification, is employed in the colloquial sense in which the expressions are generally used in this art, meaning "sedimentation".

For improved fractionations or purifications it is possible to fractionate a mixture repeatedly, either by repeated fractionation steps in accordance with the present invention or by a combination of such fractionation step with other conventional fractionation steps.

When a polyalkylene glycol, more particularly polyethylene glycol (PEG) is used as the precipitant, it is preferred to employ a commercial preparation "polyethylene glycol 6000", the code number being by approximation indicative of the molecular weight. Thus, polyethylene glycol 6000 as supplied by Shell is stated by those manufacturers as having an average molecular weight between 6000 and 7500, according to the determination methods employed by the manufacturers. In any event the molecular weight of the precipitant is not very critical and minor variations in optimum concentration of PEG due to that parameter are easily determined by a routine experiment, such routine experiment for example, following the general pattern of analogous routine experiments described in U.S. Pat. No. 3,415,804. Other suitable polyalkylene glycols which may be used instead of or in addition to polyethylene glycol are the polymers of low molecular weight homologues of ethylene glycol, in particular propylene glycol or mixed polymers of polyethylene glycol and such homologues, the preferred molecular weight limits being substantially similar to those described for polyethylene glycol, the upper limits being determined primarily by viscosity considerations.

In accordance with preferred embodiments of the process, the separation of antibodies from the egg yolk involves at least two steps, preferably at progressively increasing conditions of precipitating power of the contents of admixed precipitant as above defined, that is the linear filamentary non-charged polymer precipitant, the initial precipitating power being adjusted to remove easily precipitated impurities, in particular caseinous protein, without precipitating the antibodies, followed by an increase in precipitating power to selectively precipitate the antibodies.

When the precipitant is PEG 6000, the first precipitation step for removing the caseinous protein should be carried out at more than 3% and less than 4% by weight of PEG 6000 by weight based on the volume of aqueous yolk. Preferably the yolk is diluted with between one and ten parts, more preferably between 1.5 and 5 parts, preferably 2 parts by volume of water, the water being for example, buffered to a pH of between 6 and 8, e.g. between 6.5 and 7.8, say 7.5.

The correct choice of precipitant concentration during that first precipitation stage is rather critical. Unless the concentration of PEG 6000 is higher than 3%, the precipitation of caseinous protein may be unsatisfactory, whilst unless said PEG concentration is less than 4%, there may be losses of desired antibody. The preferred concentration of PEG is between 3.3 and 3.7%, more particularly 3.5%.

The second precipitation step, if carried out with PEG 6000, is found to take place most satisfactorily at concentrations higher than 11% (below which there occurs losses of antibody) and lower than 14%, the concentration at which contaminating substances such as albumen and various undesired proteins are inclined to be coprecipitated. The preferred concentration is between 11.5 and 12.5%, more particularly 12% weight per volume.

The step of lipid removal may take place by extraction with an organic solvent such as toluene which includes a risk of damaging the sensitive IgY antibodies. However a very effective and simple method comprises first mixing the aqueous diluted egg yolk with the amount of linear filamentary non-charged polymer precipitant required for precipitating caseinous protein contained therein and then filtering the resulting supernatant on the surface of which floats the lipid layer, through an absorbent filter plug adapted to retain the lipid layer. An absorbent cotton plug is suitable as such absorbent layer.

The antibody concentrated obtained by the second precipitation step is preferably subjected to further purification, e.g. by being predissolved in an aqueous medium, followed by renewed precipitation of the antibody, e.g. with alcohol or other suitable protein precipitants, but preferably again with a linear filamentary non-charged polymer precipitant as above defined, e.g. PEG.

For many, if not most purposes the presence of traces of PEG is not considered objectionable. However, if it is objectionable, it is possible to employ a non-objectionable precipitant in the last precipitation stage. Alternatively, if PEG is used for further purification, the immuno globulin concentrate may be freed of PEG by redissolution and precipitation with ammonium sulphate employed at half its saturation concentration.

The temperature at which the process is carried out is not very critical, ranging preferably between 0° and 30° C., more preferably between 4° C. and 25° C., e.g. ordinary room temperature.

The above process is suitable for recovering the antibodies not only in good yields, but also in very pure form, such that in appropriate cases the product can be injected into animals or humans with little or no danger of allergic reactions. It is furthermore believed that, because soft-boiled eggs form such a normal part of human diets, a majority of humans have become desensitised to otherwise allergenic substances present in egg yolk, and which might still be present in trace amounts in the product in accordance with the invention.

Surprisingly the above described method of concentrating or purifying IgY antibodies can even be adapted to the separation of different IgY antibodies from one another. Thus there is provided a process as aforesaid which includes a step of concentrating or purifying a specific IgY fraction selected out of the total of the IgY antibodies recovered from the yolk, comprising thoroughly mixing recovered mixed IgY antibodies containing the selected specific IgY antibodies in addition to other IgY antibodies of the total with water, adjusting the pH of the water to a predetermined level in or around the isoelectric pH range of the recovered antibodies and with an amount of water-soluble, linear, filamentary, non-charged polymer (as defined and explained above) sufficiently large to attain only partial suppression of the solubility or dispersibility of the antibodies, followed by the formation and separation of two phases:

A. an aqueous phase wherein a substantial part of the IgY antibodies is dissolved or dispersed, B. a displaced non-dissolved or non-dispersed phase containing the remaining part of IgY antibodies, one of the phases containing the selected specific IgY antibodies in greater proportion (based on antibody content) than the recovered mixed antibodies; and recovering the antibodies of that phase.

For example, the selected antibodies may be in greater proportion in the aqueous phase (A) in which case the pH of the aqueous phase is adjusted to a level closer to or substantially equal to the isoelectric pH of the selected specific antibodies followed by precipitating the selected antibodies at that pH and recovering the precipitated antibodies. The precipitation may result entirely from the pH adjustment or, particularly if higher yields are desired, may be promoted by increasing the concentration of the polymer.

This important fractionation method can be adapted successfully also to the separation from one another of other antibodies of a given class of antibodies, e.g. mammalic IgG antibodies. This is important in the context of the present invention particularly in the light of certain embodiments wherein IgY antibodies produced in accordance with the present invention are used to elicit in mammals IgG antibodies against such IgY and where it is desired to purify and concentrate the specific anti-IgG antibodies, e.g. for certain immuno-assay preparations.

Accordingly this specific aspect of the invention in a more general sense provides a process for concentrating or purifying specific antibodies from a mixture comprising such specific antibodies in addition to other antibodies belonging to the same antibody class as do the specific antibodies, which comprises thoroughly mixing the mixture with water, adjusting the pH of the water to a level in or around the isoelectric pH range of the mixture of antibodies and with an amount of water-soluble linear filamentary non-charged polymer sufficiently large to attain only partial suppression of the solubility or dispersibility of the antibodies, followed by the formation and separation of two phases (A) and (B) and the recovery of the specific antibodies from one of those phases as specifically set out in the preceding three paragraphs. If the antibodies are IgY antibodies recovered from egg yolk, the phase separation is generally carried out at a pH between 4 and 6 or slightly higher, the isoelectric pH of IgY being in the region of 5.8. If the antibodies are mammalic IgG antibodies, the pH is between about 5 and 7 or slightly higher in view of the isoelectric pH of mammalic IgG antibodies being in the region of 6.8.

The above fractional precipitation of closely related antibodies from one another is based on the important new discoverey that antibodies elicited against immunogens of relatively low molecular weight have their minimum solubility at a pH which is lower than that at which antibodies elicited against relatively large immunogens have their minimum solubility.

Therefore, for selectively insolubilising first antibodies of the mixture which have been elicited against immunogens of relatively low molecular or particle weight whilst selectively leaving in aqueous solution or dispersion second antibodies of the mixture being antibodies against immunogens of higher molecular or particle weight than the immunogens of relatively low molecular weight, the invention provides that the pH is adjusted to a level below the isoelectric pH for the second antibodies and adjusting the amount of the polymer to attain the partial suppression at that level.

On the other hand, for selectively insolubilising second antibodies of the mixture which have been elicited against immunogens of relatively high molecular or particle weight whilst selectively leaving in aqueous solution or dispersion first antibodies of the mixture being antibodies against immunogens of lower molecular or particle weight than the immunogens of relatively high molecular weight, the procedure provides for adjusting the pH to a level above the isoelectric pH for the first antibodies and adjusting the amount of the polymer to attain the partial suppression at that pH level.

The manufacturing process and the products of the process can be applied to the passive immunisation of a mammal, the term including humans, against disease, poisoning or another pathological condition against or from which the immunisation is to afford protection or relief. In that case the immunogen used for actively immunising the fowl carries immunogenic determinants adapted to specifically elicit IgY antibodies which can bind antigens which give rise to the pathological condition. The resulting IgY antibodies after having been recovered from the egg yolk are converted into an injectable form and are then injected into the mammal in an immunising dosage. The concept of passively immunising mammals including humans with fowl egg IgY is considered novel per se.

It is comparatively easy to raise and keep chickens under conditions where they will be exposed substantially only to the antigens against which immunity is desired. It is particularly advantageous that this immunity persists over such long periods, such as the entire laying period without subsequent booster doses of antigen being necessary.

Thus the invention may be applied to the production of antivenoms, e.g. against snakes, scorpions and spiders. The reduced danger of allergic reactions is a particular advantage, as is the adaptability of the process to produce anti-venoms against the rarer species of snakes or snakes against which anti-venoms are not yet readily available from other sources. Particular examples are tree-snakes (boomslang) bird snakes, vine snakes and even mambas.

Such anti-venoms, derived from birds' eggs are considered novel per se.

The invention is also particularly suitable for the manufacture of antibody concentrates for the detection and identification of various antigens in the laboratory, e.g. for pathological or forensic purposes.

The invention may also be applied to the manufacture of polyvalent antivenines.

It is also suggested to employ the invention for the production of anti-fetal protein antibodies for diagnostic purposes in certain malignancies, i.e. liver cancer and other cancers, for the manufacture of anti-lymphocytic sera for use in organ transplantation, anti-fetal protein antibodies for possible treatment of malignancies and all types of anti-sera against any antigens for whatever purpose these anti-sera may be required.

As regards the process it would be within the scope and spirit of the present invention to reverse the sequence of precipitation steps by first precipitating caseinous proteins together with the antibodies at the higher precipitant concentration, followed by lowering the PEG concentration, more particularly by adding aqueous liquid, thereby to redisperse the anti-bodies whilst leaving the caseinous proteins precipitated, and finally if so desired to reprecipitate the antibodies from the supernatant.

Where the immunological preparations produced in accordance with the present invention are used diagnostically, more particularly where an antigen used in the immunisation of hens is associated with a pathological condition to be diagnosed, the antibodies separated in accordance with the invention, are applied to a pathological test sample and a precipitin reaction between the antibodies produced and the corresponding antigens in the test sample is observed in a manner which may be substantially as known per se. One technique is the well-known Ouchterlony technique, which requires no detailed description, since it is well-known in the literature and from standard textbooks. As a general rule it is preferred for the said technique to be carried out at a substantial sodium chloride concentration in the gel in which the test is carried out, which gel is preferably agarose gel. Suitable sodium chloride concentrations are generally between 0.1 and 0.2M, usually 0.15M is preferred which is readily tolerated by the sensitive substances such as viruses. Higher concentrations are used only if no or no satisfactory precipitin reaction is observed in which case the concentration may be used to preferably not exceed 1.5M. This may yield better reactions with antigens of mol. weights less than 150000.

A useful description of double diffusion techniques and in particular of the Ouchterlony method can be found in "Methods in Immunology and Immunochemistry" edited by C. H. Williams and Merrill W. Chase, Academic Press (1971), Vol. III, pages 146–161.

Although the above reference recommends the use of either agar or agarose as gel medium for the test, agarose was found to be substantially more suitable in the context of the present invention because of white haloes formed around the yolk immuno-globulin (IgY) wells in agar (possibly due to a reaction product between agaropectin and residual traces of Lysozyme).

However, the Ouchterlony test, even when carried out at relatively high sodium chloride concentrations, is not preferred for use with IgY preparations according to the present invention when of particularly high uniformity—as is readily attainable according to the invention as one of the advantages thereof. In that case the Ouchterlony technique may fail to produce a visible reaction. For that reason it is preferred to employ one of the numerous binding assays known in the art. The same applies in the case of determining relatively small haptens. Suitable techniques include radio-immuno assays and enzyme-linked immuno assays (ELISA). Also suitable are precipitation assays wherein the antibodies according to the present invention are used in combination with a further precipitant, e.g. ammonium sulphate or polyethyleneglycol or the like. The principles of those techniques are known to persons skilled in the art and require no further description.

DESCRIPTION OF PREFERRED EMBODIMENTS AND EXAMPLES

In the following the invention will be further described with reference to some preferred examples. For the sake of consistency all examples are carried out using the same precipitant PEG 6000. However, in the light of the preceding description a person skilled in the art can readily apply the examples to different precipitants. The examples are chosen to give a fair and representative cross-section of practical applications of the invention to enable the person skilled in the art to practise different, but analogous embodiments.

EXAMPLE 1

Hens

White Leghorn and Rhode Island Red-White Leghorn hybrids, 20 weeks old, were kept in isolation for immunoglobulin and egg production. They showed no sign of illness or discomfort during the period that they were involved in the experiments.

Chemicals

Polyethylene glycol MW 6000 daltons (PEG) was used in the fractionation of the egg yolk. Sodium azide at a concentration of 0.1 g/liter was used as a preservative of the washed yolks and of the finally purified yolk immunoglobulin (IgY).

Buffer

The yolks were diluted in 0.01M phosphate buffer of pH 7.5 which contained 0.1M NaCl. Buffer of the same composition was used as the dispersion medium for the IgY when finally purified.

Immunisation

The pullets received an initial intramuscular injection with each of the antigens in phosphate buffer of pH 7.5 emulsified with an equal volume of incomplete Freund's adjuvant. The concentration of antigen used was not critical and varied from one antigen to another, but was generally in the range of 1 to 5 mg/ml. After the initial injection the young hens received a further three injections spaced at weekly intervals, each injection had a volume of 1 ml and thus corresponded to between 1 and 5 mg of antigen. A stage of hyperimmunisation was reached. Eggs were collected, labelled and stored at 4° until processed for extraction of IgY. This was continued over a period of 9 months.

More consistent results are attained if the injections are repeated twice weekly for the first three weeks, thereafter weekly, and after the attainment of a plateau-like levelling-off of the antibody level in the serum of the hen at monthly intervals. The plateau-like levelling-off is usually attained after about three to four weeks. This may even result in continued rise in the IgY content of the egg yolk long over the levelling-off stage.

It is furthermore preferred to divide each injection in 0.5 ml portions over two injection sites (preferably the two breast muscles) and to administer after the first injection 0.5 ml of 1:5 diluted adrenaline subcutaneously 10 minutes prior to each inoculation as a precaution against anaphylactic shock.

Extraction and purification of IgY

Several methods for separating the lipoidal matter and casein-like protein from diluted yolk were compared. These involved the use of organic solvents such as ether and toluene and precipitation with ammonium sulphate. Best results were obtained by displacement with PEG.

The method of separation of IgY was remarkable in its simplicity. All of the following is done at neutral pH (6.5–7.8) for which reason it is preferred to use a dilute phosphate buffer (0.1M) as the aqueous medium throughout the process. The yolks collected from a number of eggs were thoroughly washed in a weak jet of distilled water to remove all the albumen. The yolks were dropped into a large glass funnel supported on a measuring cylinder. The fall into the funnel causes the yolk sacks to break and release the yolk which collects in the cylinder. The volume of yolk was measured and a volume of buffer equivalent to two volumes of yolk was added and thoroughly mixed.

PEG which had been finely pulverised in a Waring blender was added to a final concentration of 3.5% by weight of polymer to volume of diluted yolk. The mixture was stirred until all the polymer was dissolved. The mixture was centrifuged in a Sorvall centrifuge at 10000 rpm (12,000×g) for ten minutes. This operation caused the separation of three phases in the centrifuge tubes. These were, a yellow fatty layer on the surface, a clear supernatant layer occupying the largest volume and a semi-solid pliable layer of the bulk of the yolk and caseinous protein "pellet" representing approximately ⅓ of the total volume of substance in the centrifuge tube. The supernatant fluid with the fatty layer was carefully decanted into a funnel containing an absorbent cotton plug in the neck of the funnel. This plug filtered off the lipid layer that was decanted with the supernatant fluid. The volume of the clear filtrate was measured and pulverised PEG was added by gentle stirring to a final polymer concentration of 12 g PEG in 100 ml yolk extract. At this concentration the PEG caused complete displacement of the IgY. A certain percentage of associated proteins notably α and β livitin coprecipitated with the IgY. The precipitate was centrifuged off at 10000 rpm in a Sorvall centrifuge. The pellets were redissolved to the original volume in phosphate buffer and the IgY once more precipitated with 12% pulverised PEG and centrifuged. The pellets obtained were compacted by subjection to a centrifugal force at 10000 rpm and the exuded solution of PEG originally entrapped in the pellets was removed by suction. The pellets were compacted once more and residual PEG solution discarded. In this manner the polymer which contaminated the IgY was reduced to a level at which it could not interfere with the antibody antigen reaction. The final pellets were dissolved in a volume of phosphate buffer equivalent to half the volume of yolk from which it was derived. The protein concentration in the final product was of the order of 6 mg/ml. Sodium azide (0.01%) was added as a preservative. Sodium azide may also be incorporated earlier, namely in the buffer used for diluting the yolk (see above) in 0.01% concentration. By dissolving the pellets in a smaller volume, more concentrated solutions may be obtained if desired.

Optionally the IgY may be freed of traces of PEG by precipitation of the IgY with half saturated ammonium sulphate followed by centrifugation. The PEG forms a liquid phase in the aqueous ammonium sulphate phase, while the IgY forms a third phase on the bottom of the centrifuge tube.

Rate of introduction of antibodies into the yolk following immunisation

The rate of transfer of antibodies from the hen to the yolk was followed in three systems:
1. $\beta$ Nudaurelia virus-anti$\beta$ Nudaurelia virus IgY,
2. Amandin-anti amandin IgY, and
3. Tetanus toxin-anti tetanus toxin.

Purified IgY isolated from individual eggs laid on alternative days were tritrated for their ability to precipitate the antigens in Ouchterlony gel diffusion in the cases of $\beta$ Nadaurelia virus and amandin. The neutralising activity of anti tetanus IgY was tested in Swiss white mice. In all cases it appeared that the antibodies appeared in detectable amounts 10 days after the initial injection. When booster injections of the antigens were given the time lapse between injection and rise in antibody titre became shorter until a level of antibody was reached which remained constant for 4 months. At this stage the experiment was terminated.

The precipitin titre of the IgY directed against $\beta$ Nudaurelia virus was estimated to lie between 1/256 and 1/512 in the yolks of the hen which responded best. The hen which responded poorest showed a titre lying between 1/128 and 1/256.

The yolks of hens immunised with amandin showed maximum precipitating titres of the order of 1/64. This titre can be improved by using the antigen in cross-linked form as described in example 7 below.

Anti-tetanus IgY neutralised 2 mld of tetanus toxin at a dilution of the IgY which varied between $10^{-4}$ and $10^{-5}$. After the injections of the hens had stopped this level of activity was maintained in the yolks for the entire period of the experiment which lasted four months. It was observed as a general rule that the IgY in the egg yolks rises to higher levels than in the hen serum. It has the same molecular weight as in serum (170000).

EXAMPLE 2

Yolk antibodies (IgY) directed against viruses of plants

Example 1 was repeated using plant viruses as antigens. The appearances of anti plant virus antibody in the yolks followed the same patterns as with Nudaurelia virus, amandin and tetanus toxoid. The titre obtained with IgY against tobacco mosaic virus was of the same order as that usually obtained with antiserum raised in rabbits.

Bromoegrass mosaic virus IgY antibodies produced double lines of precipitate in Ouchterlony plates. The lines closest to the antigen well are caused by intact virus particles and the ones near the central antibody well are caused by viral protein subunits.

Turnip yellow mosaic IgY antibodies produced only precipitin lines corresponding to intact virus particles and the titre of the IgY antibodies was similar to the titre of immune sera from rabbits.

Similar results were obtained with Sunn-hemp virus, Broadbean mosaic virus and Cowpea Chlorotic Mottled virus.

The antibody solutions, stabilised with sodium azide can be kept for prolonged periods at 4° C. for use as a diagnostic reagent, employing standard tests, more particularly double diffusion tests of which the Ouchterlony is preferred which is preferably carried out on agarose plates.

EXAMPLE 3

Diagnosis of Bromegrass mosaic virus (BMV)

Bromegrass mosaic virus (BMV) is shown to be present in infected extracts of wheat and barley by the Ouchterlony double diffusion technique in which the IgY type of antibody directed against BMV and produced in accordance with example 2 above, is placed in a well cut into agarose contained in a Petri dish. The test sample of antigen derived from the infected extracts of wheat and barley is placed in wells cut in a circle round the central well and about 5 mm from the central well. 4 to 6 such wells are cut around the central well in the manner well-known from standard literature. The Petri dishes with the reactants in the wells are left at room temperature for 24 to 48 hours. During that period the reactants (namely the diagnostic agent IgY and the BMV antigen of the sample) will diffuse from their respective wells into the surrounding agarose gel to form visible lines of precipitates between the central well and the surrounding wells. These typical precipitate lines confirm the presence of BMV antigen in the test sample, to serve as a positive diagnoses of BMV in the wheat or barley.

Although this is not always necessary, it is a preferred technique to incorporate a concentration of beween 0.15 and 1.5M sodium chloride in the agarose gel which often helps to improve the sensitivity of the test. This is less necessary with viral material than with other types of antigens, particularly those of lower molecular weight. The preferred concentration as a standard technique is 0.15M (which concentration in the case of viruses is preferably not exceeded). Higher concentrations are preferably selected only if at 0.15M the observed precipitin response is weak or unobservable.

EXAMPLE 4

IgY antibodies against human IgG

Human and rabbit IgG have a similar low mobility in the electric field and consequently are moved towards the negative pole when subjected to electrophoresis in agarose or agar gel. In contrast, IgY has an appreciably higher mobility towards the positive pole. Because of this difference in mobility, the possibility presented itself of overcoming the difficulties that are found when various antigens of low mobility such as human IgG are analysed by one and two dimensional Laurell electrophoresis. Because of the considerable endosmosis that occurs with IgG, it is necessary prior to electrophoresis to alter the charge on the antibody molecules by chemical reaction; some with IgY antibody, such additional chemical modification is not necessary.

It is important in clinical diagnosis to know the level of human IgG in blood circulation. This can be established by the extent to which human serum may be diluted to give a precipitate line against IgY antibody produced in the hen against IgG in accordance with the procedure described in Example 1 and using an antibody preparation extracted from the hen's yolk as described in Example 1.

EXAMPLE 5

Clinical determination of human IgM

It is important in clinical diagnosis to know the level of human IgM. This is an antibody which occurs early during immunisation, especially against bacteria and viruses. Hens are immunised with pure IgM in accordance with the procedure described in Example 1. The IgY antibody against this IgM is recovered from the egg yolks as described in Example 1 and serves as a reagent for the clinical diagnosis using known double diffusion procedures.

EXAMPLE 6

Tetanus antitoxin is prepared by the procedure described in Example 1. The molecular weight of the neurotoxin of Tetanus toxin as produced by the Tetanus organism is of the order of 145000 and is sufficiently high to produce good antibody yields in hens. Titres of up to $10^{-5}$ mld/ml (minimum lethal dose) with 6 mg IgY/ml are attained. For injection purposes this will be equivalent to the anti-serum conventionally prepared in horses. The IgY recovered from the yolks by the procedure of Example 1 is converted into injectable form as follows:

Traces of PEG are removed from the IgY concentrate by precipitation with 40% alcohol at 0° to 4° C. The IgY precipitate is centrifuged off and freed of alcohol by freeze drying. The resulting powder is then dissolved in the minimum volume of saline. The resulting injectable antitoxin serves as an alternative to horse antitoxin for use in humans who are allergic to horse serum. The dosage is chosen in the same manner as with horse serum antitoxin, depending on the condition of the patient to be treated.

EXAMPLE 7

Snake antivenine (Cobra, Naja Nivea). The venom of this Cobra is composed of at least 20 components, all of which have molecular weights well below 30000, more particularly in the range between 3000 to less than 30000. These components are therefore poor antigens for hens. By cross-linking the venom components with glutaraldehyde, large aggregates are formed through covalent bonding. When these aggregates are injected into hens, they exhibit a higher order of antigenicity. The cross-linkage of the venom components occurs in a random manner, and the different components are represented as antigenic groups on the surfaces of the cross-linked aggregates. Cobra venom is particularly suitable for such cross-linkage as the components are very basic and react well and rapidly with glutaraldehyde in the following procedure:

Between 1 and 10 mg of dried venom is dissolved in 1 ml 0.1M sodium chloride. Glutaraldehyde is added to a final concentration of 0.6%. The excess glutaraldehyde is dialysed off, using conventional cellophane dialysis tubing. The precipitate is stored for immunisation purposes. The immunisation and recovery of antibody proceeds in accordance with Example 1.

Testing of the antibody product reveals the following: the total antibody titre has been improved by the cross-linking step. However, the antitoxic effect is not yet adequate against some of the 20 or more venom components. The preparation therefor requires to be combined with antivenine concentrates having a selective activity against those additional venom components. An alternative approach is to prefractionate the venom by known techniques (e.g. PEG fractionation, exclusion chromatography) and to prepare antivenines against the individual fractions the techniques being optimised individually for the different fractions) and the different antivenines are then combined in a ratio to produce a preparation effective against the full range of venom components.

EXAMPLE 8

Snake antivenine—Puffadder

Puffadder venom is of less diverse composition than cobra venom (Example 7), the components being moreover of higher molecular weight. After cross-linking as described in Example 7, the resulting antigen preparation can be used in the manner of Example 1 to produce an antivenine preparation.

EXAMPLE 9

Cancer diagnosis

Anticarcino embryonic antigens from human digestive tumours are cross-linked as described in Example 7, and the cross-linked aggregates are used as antigens for the production of IgY antibodies for diagnostic purposes as more fully described in Example 1. In the present example carbodiimide cross-linking agent (concentration 0.1%) is used which cross-links the carboxyl groups of the antigens.

The same procedure is adopted with $\alpha_1$—fetal protein from liver cancer (haepatoma) used in the production of IgY antibody for diagnostic purposes in accordance with the procedure of Example 1. It is necessary to cross-link these antigens as their molecular weights are too low for satisfactory immunological response in the hen.

EXAMPLE 10

Serameba antigen antibodies

Serameba antigen is a mixture of at least 19 antigens and is used for the diagnosis of amoebiasis. The molecular weights of these antigens are low. Accordingly the cross-linking procedure according to Example 7 is adopted before the hens are immunised in accordance with Example 1 for the production and recovery of the antibody preparation.

EXAMPLE 11

Haemocyanin

Haemocyanin antigens of *Burnupena cincta* have a molecular weight of $8 \times 10^6$ and are directly suitable for the immunisation of hens in accordance with the procedure of Example 1.

The same applies to Haemocyanin antigens of Jasus lalandii, molecular weight $5 \times 10^5$.

EXAMPLE 12

Haemocyanin used as a carrier molecule

Haemocyanin is produced as described in example 11. Methionine 5-encephalinsulphoxide is covalently bonded to the haemocyanin as described by J. A. King and R. P. Millar in Peptides Vol. 1, page 211-216 (1980). This substance is used as an immunogen for immunising hens according to example 1, followed by recovery of the IgY antibodies. The IgY antibodies are used in an RIA test as described in the aforesaid reference.

EXAMPLE 13

IgY antibodies against $T_3$-protein conjugates

Triiodothyronene ($T_3$) is conjugated to chicken albumen as described by Hossein Gharib et alia in J. Clin. Endocr. 33, 509 (1971) using a carbodiimide coupling compound. The conjugate is used to immunise hens, followed by recovery of the IgY antibodies against $T_3$ as described in example 1. The antibodies can be used in a radio immuno assay procedure as described in that reference.

EXAMPLE 14

Grafting of digoxin onto naked bacteria

In order to introduce a reactive amine group into digoxin, the substance is first subjected to periodate oxidation and then reacted with hexamethylenediamine as follows: 109 mg of digoxin (0.14 milli mol) are suspended in 10 ml absolute ethanol at room temperature. 5 ml of 0.1M $NaIO_4$ are added dropwise with magnetic stirring. After 25 minutes 1.5 ml of 1M ethyleneglycol is added.

5 minutes later the reaction mixture is added dropwise, with magnetic stirring to 2.44 g (0.02 mol) of hexamethylene diamine in 10 ml of water and of which the pH had previously been adjusted to 9.5 with 5% potassium carbonate. The pH is maintained in the 9.0 to 9.5 range by the dropwise addition of 5% potassium carbonate or 0.1M HCl respectively. After 45 minutes the pH is stable and 0.075 g of sodium borohydride, freshly dissolved in 5 ml water is added. 16 hours later the pH is lowered to 6.5 with 1M formic acid. After 1 hour at pH 6.5 the pH is raised to 8.5 by the addition of 1M ammonia.

The reaction mixture is then dried with a rotary evaporator and the residue is taken up in a mixture of chloroform and ethanol (1:1) and purified on silica gel using a chloroform-ethanol mixture (3:2) as eluent. In this manner an amino group is introduced into the digoxin molecule after conjugation with hexamethylenediamine.

The naked bacteria are prepared as follows

*Salmonella minnesota* R595 is cultured in an aqueous growth medium having the following composition per liter:

15 g peptone, 5 g yeast extract, 3 g NaCl, 2 g $Na_2HPO_4.12H_2O$, 0.2 g $MgSO_4.7H_2O$, 10 g glucose.

The bacteria are incubated for 7 days at 37° C.

Thereafter phenol is added (final concentration 1%) to kill the cells. The cells are separated off and washed repeatedly: first twice with distilled water, then twice with acetone and then once with ether followed by drying in vacuo. This product can be stored at room temperature until required.

For the hydrolysis in order to strip off O-antigenic determinants, the dry bacteria are washed twice with 1% acetic acid and are then suspended in 1% acetic acid (1 g/ml) and heated to boiling for two hours.

The bacterial particles are separated and washed twice with distilled water followed by drying in vacuum. The dried powder constitutes the naked bacterial material.

The amine derivative of digoxin is then bonded covalently onto the naked bacteria as follows:

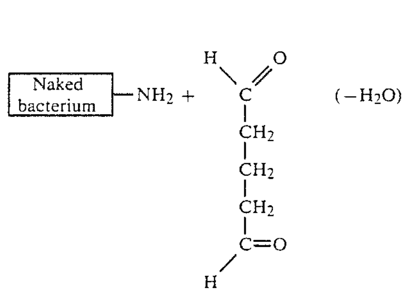

-continued

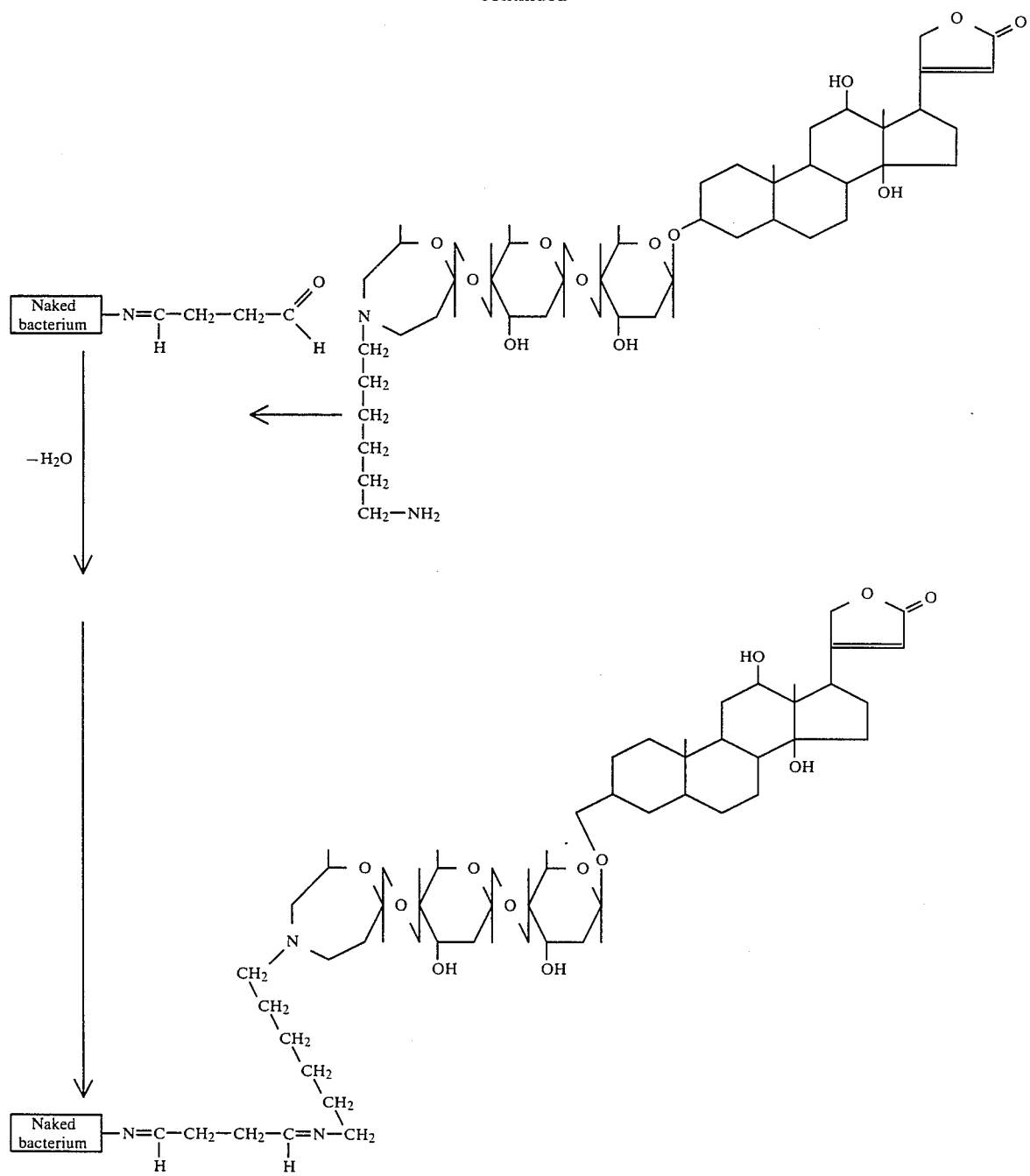

Digoxin naked bacterium conjugate 30 mg of the dried naked bacteria are reconstituted by being suspended in 6 ml water and incubated for 1 hr at 37° C. The supernatant is centrifuged off at 12000 g. 6 ml 0.25% aqueous glutaraldehyde solution is added to the bacteria followed by 1 hour incubation at 37° C. in turn followed by centrifuging off the supernatant at 12,000 g.

The reaction product is reacted for one hour at 37° C. with 1 ml of a 1% solution of digoxin derivative in dimethyl sulphoxide (DMSO) or methanol, followed by centrifugation at 12000 g. The sediment is then reacted for 1 hour with 4.8 ml of 0.33% aqueous ethanolamine at 37° C. to block off the remaining aldehyde groups. The product is centrifuged at 12000 g and washed twice with 6 ml portions of water, each time followed by centrifugation at 12000 g. The product may then be suspended in 18 ml phosphate buffered saline solution (PBS) for use in immunisation of hens and IgY recovery as described in example 1.

EXAMPLE 15

Grafting of T3 (triiodothyronine) onto naked bacteria 30 mg of naked bacteria are prepared as in Example 1 suspended in 6 ml of water and incubated for 1 hour at 37° C. to allow the bacteria to swell. The suspension is then centrifuged for 10 minutes at 12000 g to remove the supernatant.

6 ml 0.25% glutaraldehyde aqueous solution is added followed by incubation for 1 hour at 37° C. Again the suspension is centrifuged for 15 minutes at 12000 g to remove the supernatant.

1 ml of a 1% methanolic solution of the sodium salt of triodothyronine is added followed by incubation for one hour at 37° C. and centrifugation for 10 minutes at 12000 g to remove the supernatant.

4.8 ml 0.33% ethanol amine solution is added followed by incubation for one hour at 37° C. and centrifugation for 10 minutes at 12000 g to remove the supernatant. The product is shaken up with 6 ml water and again centrifuged as before, followed by adding once again 6 ml of water and repetition of the centrifugation to remove the supernatant. The product is then taken up in 18 ml of phosphate buffered saline solution for immunisation and IgY recovery as in Example 1.

EXAMPLE 16

Preparation of T4 (tetraiodothyronine) bonded to naked bacteria

The procedure is the same as in example 2 except that teraiodothyronine is substituted for triiodothyronine.

EXAMPLE 17

Bonding of thyroxine onto naked bacteria

The present example serves to illustrate the use of cyanogenbromide as a linking compound.

First the naked bacteria are "activated" with cyanogenbromide (CNBr) as follow:

2 mg of a 25 mg/ml solution of CNBr is placed in a suitable titration holder, magnetically stirred, and the pH is adjusted by means of a pH-stat apparatus, using a 2M sodium hydroxide solution for the adjustment of the pH to 11.5.

50 mg of naked bacteria are suspended in one ml water and allowed to swell for one hour at 37° C. The suspension is then added to the abovementioned reaction mixture and the reaction is allowed to proceed for 6 minutes, during which time the pH is kept constant at 11.5. The naked bacteria are then washed on a sinter glass filter with water. These pretreated naked bacteria can now be stored at −10° C. until required for the next step.

The antigen is bonded to the activated naked bacteria as follows:

1 ml of 1% thyroxine solution is added to an amount of suspension containing 30 mg of naked bacteria activated as described above. The mixture is incubated overnight and then centrifuged for 10 minutes at 12000 g to remove the supernatant. The sediment is resuspended in 4.8 ml 0.5M $NaHCO_3$ solution and centrifuged. The supernatant is discarded. 4.8 ml of a 0.33% ethanol-amine solution is added. The mixture is left for one hour and then centrifuged. The supernatant is discarded. 6 ml 0.01M HCl are added followed by centrifugation and discarding the supernatant. This step is repeated once with 6 ml 1M NaCl and twice with 6 ml of water. The washed sediment is dried completely on a rotary evaporator and taken up in 18 ml phosphate buffered saline solution of immunisation and IgY recovery as described in Example 1.

Exactly the same procedure can be followed for coupling $T_3$ instead of $T_4$ to naked bacteria.

EXAMPLE 17

Antibodies against IgG

Rabbit immunoglobulin is bonded to naked bacteria with glutaraldehyde using the procedure described in Example 15. This carrier-bonded immunoglobulin is then used for the immunisation of leghorn hens as described in Example 1 and the antibodies are recovered as described in Example 1.

For purposes of comparison the immunisation and recovery of antibodies is repeated on similar leghorn hens using human IgG which had not been bonded to any carrier as the immunogen. The antibody yield as reflected in the agglutination titre for the naked bacteria bonded IgG was four dilution levels higher than for ordinary IgG.

EXAMPLE 18

Alpha-fetoprotein antibodies

Alpha-fetoprotein antibodies are commercially valuable because they are useful for large-scale screening of pregnant women (e.g. by RIA techniques) for spina bifida and anencephaly in the fetus.

Alpha-fetoprotein (AFP), molecular weight 70000 daltons, is synthesised first by embrionic yolk sack cells and later by fetal liver cells. It is the first alpha-globulin to appear and is the dominant seral protein of very early mammalian embryogenesis. During pregnancy some AFP is normally excreted into the amniotic fluids in the urine of the second trimestal fetus and is slowly removed by fetal swallowing. Much higher concentrations of AFP are found in the amniotic fluids of fetuses with open neural tube defects. As a result of movement of AFP across the placenta, the maternal serum AFP concentrations increase during pregnancy. Assays for AFP in maternal sera can therefore give an indication of these open neural tube defects of a fetus at an early stage during pregnancy.

There are large structural similarities between albumin and AFP. Any useful assays must be able to distinguish clearly between the two substances. In preliminary experiments attempts were made to immunise some fowls against albumin and some against AFP. The immungenic response was too small to produce useful concentrations of IgY against these immunogens in the egg yolks. Both substances were then coupled to naked bacteria by the procedure described in example 14. Hens were immunised with the resulting immunogenic materials according to the procedure of Example 1. In both cases good yields of antibodies were obtained having high avidities. The K-value for IgY anti-AFP antibodies was found to be $2 \times 10^{11}$ L/mole. The best commercial product which could be found uses rabbit IgG-anti-alpha-fetoprotein having a considerably lower avidity namely $6.0 \times 10^9$ L/mole.

The K-value for the IgY anti-albumin antibodies was found to be $5.5 \times 10^{11}$ L/mole. There was no cross reaction between the anti-AFP antibodies and albumin. There was a small degree of cross reaction of the anti-albumin antibodies with AFP. However, this is unimportant in the present context. It was found that the anti-AFP antibodies could be used to construct a precipitation RIA quite easily and that this RIA has the necessary sensitivity and repeatability.

EXAMPLE 19

Periodate oxidation of digoxin and coupling to naked bacteria 430 mg of digoxin (0.56 mM) are suspended in 20 ml absolute alcohol at room temperature. 20 ml of 0.1M sodium metaperiodate is added dropwise with magnetic stirring. After 25 minutes 0.6 ml of 1M ethyleneglycol is added. 5 minutes later the reaction mixture is added dropwise with magnetic stirring to 600 mg of naked bacteria (see example 14) in 20 ml of water which had previously been adjusted to pH 9.5 with 0.4 ml of 5% potassium carbonate. The pH is maintained in the 9.0–9.5 range by the dropwise addition of 2 ml 5% potassium carbonate. After 45 minutes the pH is stable and 0.4 g sodium borohydride, freshly dissolved in 20 ml of water is added. 3 hours later 7.6 ml of 1M formic acid is added to lower the pH to 6.5. After one further hour the pH is raised to 8.5 by the addition of 1.5 ml 1M ammonia. The entire reaction mixture is then centrifuged for 10 minutes at 10 000×g and the supernatant is removed. The pellet is washed three times with phosphate buffered saline (PBS), whereafter 360 ml sterile PBS is added. The resulting suspension is then used for immunisation of hens and recovery of antibodies according to Example 1.

EXAMPLE 20

Coupling of horseradish peroxidase to naked bacteria

Horseradish peroxidase is an enzyme containing a high percentage of carbohydrate which can be activated with cyanogenbromide and subsequently reacted with naked bacteria (which also have carbohydrate groups on their exterior surface) or vice versa.

2 ml of cyanogenbromide solution (25 mg/ml) is placed in a container and the pH of the solution is adjusted to 11.0 by the addition of 2M NaOH solution. 50 mg horseradish peroxidase is dissolved in 2 ml water and added to the abovementioned solution. The pH is kept constant for 6 minutes whilst the reaction proceeds. The pH of the solution is then reduced to pH 7 by the addition of 0.1M hydrochloric acid. The "activated" horseradish peroxidase is separated from contaminants by gel chromatography and is lyophilized.

5 mg of the lyophilisate is dissolved in 1 ml of phosphate buffer (pH 7.6. 0.1M), 60 mg of naked bacteria are allowed to swell for one hour in 12 ml water after which the suspension is centrifuged at 10000 g for 10 minutes. The supernatant is removed and the pellet is resuspended in 5 ml 0.1M of the phosphate buffer. The solution of activated horseradish peroxidase is then added to the naked bacteria suspension and allowed to react for 18 hours at 25° C. The suspension is centrifuged at 10 000×g for 10 minutes, the supernatant is removed and the pellet is washed 3 times with PBS. The pellet is finally resuspended in 36 ml of sterile PBS for immunisation and IgY recovery according to Example 1.

The resulting antibodies are intended for use in ELISA.

EXAMPLE 21

Reaction of carboxyl groups with amine groups $T_3$ (see example 15) can also be grafted to naked bacteria via its carboxyl groups and via the amine groups on the surface of the naked bacteria. ($T_3$ is merely used as a convenient example).

60 mg of naked bacteria are suspended in 25 ml of water and 30 mg of 1-cyclohexyl-3-(2-morpholinyl-4-ethyl)carbodiamide metho-p-toluenesulphonate (morpho-CDI) is added. 20 mg of $T_3$ in its free acid form, dissolved in 5 ml of dimethylformamide is then added dropwise whilst stirring. The pH is kept constant at 5.5 with dilute hydrochloric acid or sodium hydroxide. After 10 minutes an additional 10 mg of carbodiamide is added. The suspension is kept at room temperature with constant stirring in the dark for 18 hours. The suspension is then centrifuged at 10000 g for 10 minutes, the supernatant is removed and the pellet is washed three times in PBS. The final pellet is resuspended in 36 ml of sterile PBS for use in immunisations and IgY recovery according to Example 1.

EXAMPLE 22

Reactions of carboxyl groups with hydroxyl groups

This example serves to illustrate a case where the amine groups on naked bacteria are first succimilated so as to form carboxyl groups on the surface of the naked bacteria and serve as a reactive intermediate, e.g. for the coupling of beta-ecdysone.

60 mg of naked bacteria are suspended in 2 ml of dry dimethylsulphoxide (DMSO). Succinic anhydride (210 mg) is added in small increments to this suspension. The reaction is allowed to proceed for 38 minutes, whereafter 10 ml of water is added. The suspension is centrifuged and the supernatant is removed. The pellet is resuspended in 10 ml of water centrifuged and the supernatant is removed. This washing step is repeated twice. The resulting pellet is lyophilised for further use in the next step.

The pellet (60 mg) prepared as described above is suspended in 15 ml of dry DMSO. To this suspension 30 mg beta-ecdysone, 4-dimethyl amino pyridine (1 mg) and 1-ethyl-3-(3-dimethylaminopropyl)-carbodiimide hydrochloride (422 mg) is added. The mixture is magnetically stirred for 4½ hours. 15 ml of distilled water is then added and the resulting suspension is centrifuged at 10,000×g for 10 minutes. The supernatant is removed and the pellet resuspended in 20 ml of distilled water. This suspension is centrifuged and the supernatant again removed. The washing process is repeated twice, whereafter the naked bacteria conjugate is resuspended in 36 ml of sterile PBS for use in an immunisation and IgY recovery according to Example 1.

EXAMPLE 23

Reaction of activated carboxyl groups with primary amines

This example illustrates how activated carboxyl groups are formed by means of the esterification of carboxyl groups with N-hydroxysuccinimide.

The N-succinimidyl ester of testosterone-3-(O-carboxymethyl)ether is synthesized as described by Tantchou et alia (J. of Immunoassay, 1(1), 129–147 (1980)) on page 133. This substance is then reacted with naked bacteria as follows:

60 mg naked bacteria are swollen in 12 ml of distilled water for one hour. 0.06 mg of the N-succinimidyl ester of testosterone carboxymethyl ether are dissolved in 0,2 ml methanol. The naked bacteria suspension is centrifuged for 10 minutes at 10000×g. The supernatant is removed and the pellet is resuspended in 1 ml of water.

To this suspension add the solution of the N-succinimidyl ester of testosterone carboxymethyl ether. The reaction is allowed to proceed for 2 hours at 4° C. Add 10 ml of cold (4° C.) distilled water to the suspension. Centrifuge at 10000×g for 10 minutes and remove supernatant. Add 10 ml of PBS, resuspend pellet and centrifuge at 10000×g for 10 minutes. Repeat this washing step and resuspend the pellet in 36 ml of sterile PBS for immunisation purposes and IgY production according to Example 1.

EXAMPLE 24

Reaction of anhydrides with primary amines

Anhydrides react with primary amines forming amide bonds and resulting in the effective production of carboxyl groups in the place of amine groups.

Take 1 g of metochlorpramide and dissolve in 5 ml dry chloroform. Dissolve 0,346 g of succinic anhydride in 2 ml dry chloroform. Carefully add the succinic anhydride solution to the solution of metochlorpramide and reflux for 4 hours. Remove the chloroform and recrystallise from ethylacetate to which a small proportion of petroleum ether has been added. Approximately 1 g of succinilated metochlorpramide is formed. This is an example of succinilated derivatives of a large variety of substances which can be esterified with N-hydroxysuccinimide by means of DCC according to the method of Rudinger and Ruegg (Biochem. J. 133 538, (1973)). The resulting activated carboxylic acid derivatives are reacted with naked bacteria as described for the production of naked bacteria conjugates in the preceding examples and their use in accordance with Example 1.

EXAMPLE 25

Maleimide derivatives of antigens

Maleimide groups are introduced into antigens by means of the bifunctional reagent N-hydroxy succinimide ester of N-(-4-carboxy-cyclohexylmethyl)maleimide (Eur. J. Biochem. 101, 395 (1979)).

Take 70 mg of albumin (bovine serum albumin) and dissolve in 15 ml phosphate buffer (0.1M pH 7.0). 1.5 mg of N-hydroxysuccinimide ester of N-(4-carboxycyclohexylmethyl)maleimide is dissolved in 0,1 ml dioxane and added dropwise whilst stirring to the albumin solution. The reaction mixture is incubated at 30° C. for 4 hours after which the reactive intermediate is isolated on "Sephadex G 25" using 0.1M phosphate buffer, pH 7.0 by means of gel filtration chromatography.

This maleimide derivative is then coupled to naked bacteria via naturally occurring or chemically introduced SH-groups. If desired, additional SH groups can be introduced via the method of Klokj and Heiney (Archives of Biochem. and Biophysics, 96, 605, (1962)).

60 mg of naked bacteria containing SH groups are suspended in 5 ml 0.1M phosphate buffer pH 7.0. A solution of 5 mg of the above described maleimide derivative of albumin is dissolved in 0.5 ml 0.1M phosphate buffer, pH 7.0 and is added to the naked bacteria suspension. The reaction mixture is incubated for 20 hours at 4° C. under an atmosphere of nitrogen. The naked bacteria are then isolated by centrifugation and the pellet is washed 3 times with 0.1M phosphate buffer, pH 7.0 whereupon the pellet is suspended in 36 ml of sterile PBS for immunisation and IgY recovery according to Example 1.

EXAMPLE 26

Modification of example 25

The method according to example 25 is modified as follows in that first the maleimide derivative of naked bacteria is made and then a substance containing a thiol group is reacted with the derivative.

Take 60 mg of naked bacteria and swell for one hour in 0.1M phosphate buffer, pH 7.0. 1.5 mg of N-hydroxysuccinimide ester of N-(4)-carboxy-cyclohexylmethyl)-maleimide is dissolved in 0.1 ml dioxane and added dropwise whilst stirring to the naked bacteria suspension. The reaction is allowed to proceed for 4 hours at 30° C. after which the reactive intermediate is isolated by centrifugation and washed 3 times with phosphate buffer. The pellet is finally resuspended in 5 ml 0.1M phosphate buffer, pH 7.0. 5 mg of insulin (an example of a protein containing SH groups) is dissolved in 0.5 ml, 0.1M phosphate buffer pH 7.0 and allowed to react with the naked bacteria intermediate for 20 hours under an atmosphere of nitrogen. Finally, the insulin-naked bacteria conjugate is isolated by centrifugation and washed 3 times in 0.1M phosphate buffer, pH 7.0. The pellet is finally suspended in sterile PBS (36 ml) for use in immunisation and IgY recovery according to Example 1.

EXAMPLE 27

Coupling via disulphide exchange

In this method the antigen as well as the naked bacteria are first modified for coupling.

The reaction takes place in 3 steps:

1. Introduction of 3-(2-pyridyl dithio)propionyl (PDT) groups into antigens (e.g. proteins) by N-succinimidyl 3-(2-pyridyldithio)propionate (PDP) as follows: bovine serum albumin (BSA) is used as the antigen. 80 mg thereof is dissolved in 2 ml of water and 0.3 ml of 20 mM SPDP solution in absolute ethanol is added. The two reagents are mixed and allowed to react for 30 minutes at 25° C. after which excess SPDP reagent is removed by dialysis against PBS for 72 hours at 4° C. This results in the formation of a BSA-PDT conjugate.

2. Coupling of dithiodiglycolic acid (DTDG) to naked bacteria by means of 1-ethyl-3-(3-dimethylaminopropyl)carbodiimide (EDCI):

182 mg DTDG is dissolved in 1 ml 2M NaOH. The solution is then diluted to 25 ml by adding borate buffered saline (pH 6). 1 ml of a suspension of naked bacteria (60 mg) in borate buffered saline (pH 7 ) is added. After thorough mixing a freshly prepared solution containing 250 mg of EDCI in 2.5 ml water is added with mixing. The suspension is left at room temperature for 30 minutes with occasional swirling. The naked bacteria conjugates are then removed by centrifugation and washed three times with PBS. They are stored in 2 ml PBS at 4° C. until used.

3. The previously prepared DTDG-naked bacteria conjugate is then reduced to thioglycolyl naked bacteria with the aid of dithiothreitol (DDT):

The 2 ml DTGG-naked bacteria suspension is brought to room temperature and 1 ml of 1M DDT is added and mixed. The reaction is allowed to continue for one hour with magnetic stirring. The naked bacteria are then removed by centrifugation and washed four times with PBS and finally suspended in 2 ml PBS for coupling to DSA-PDTP.

4. Coupling of PDT-DSA to thioglycolyl-naked bacteria. 2 mg PDTP-BSA dissolved in PBS (200 μl) is mixed with 2 ml of thioglycolyl-naked bacteria suspension previously prepared and allowed to react overnight with slow magnetic stirring. The resulting naked bacteria conjugate is removed by centrifugation, washed 3 times with PBS and finally resuspended in 36 ml of sterile PBS for immunisation and antibody recovery according to Example 1.

EXAMPLE 28

Toxins coupled to naked bacteria

Cholera toxin is coupled to naked bacteria as described in example 15 modified in that 10 mg of cholera toxin in 1 ml PBS is substituted for the 1 ml of 1% methanolic $T_3$ solution.

This procedure can also be employed for preparing conjugates of snake venom.

The conjugates are used as described in Example 1.

EXAMPLE 29

Carrier bound testosterone 60 mg naked bacteria are swollen in 10 ml distilled water for 1 hour as in previous examples.

The iodohistamine ester of testosterone hemi-succinate is prepared as described by Tantchou and Slaunwhite in J. of Immunoassay, 1(1), 129–147 (1980), as described there on page 139 under the heading "Reaction of iodohistamine with activated esters". 5 mg of the ester are dissolved in the minimum volume of water, added to the naked bacteria suspension and mixed well. The suspension is exposed to ultraviolet light (wave length 211 nm—mercury lamp) for 5 minutes. After irradiation the suspension is centrifuged at 10000×g for 10 minutes. The supernatant is removed, the pellets are washed three times with 20 ml PBS and the final pellet is dissolved in 36 ml sterile PBS for use in immunisation and antibody recovery according to Example 1.

EXAMPLE 30

Diesters of dicarboxylic acids as linking reagent

A solution is prepared of 2–20 mg/ml of the diester of glutaric acid (or pimelic acid) prepared by condensation of N-hydroxysuccinimide using dicyclohexyl carbodiimide (J. Am. Chem. Soc. 86, 1839–1842, (1964)). 60 mg of naked bacteria are swollen for 1 hour in 0,1M phosphate buffer pH 7.0. The above solution (containing 1.5 mg) of the diester is added to the naked bacteria with stirring. The reaction is allowed to proceed for 6 hours at room temperature. IgY (5 mg) dissolved in 0.5 ml phosphate buffer (0.1M, pH 7.0) is added and allowed to react overnight. Unreacted reactive groups can optionally be blocked with mercapto ethylamine or ethanolamine.

The naked bacteria conjugate is recovered and washed and resuspended as in the previous examples. In this example glutaric and pimelic acid diesters of N-hydroxysuccinimide react with amine groups on protein molecules with the liberation of N-hydroxysuccinimide. The conjugate is used as in Example 1.

EXAMPLE 31

Bismaleimides as crosslinking agents

Example 30 is modified by using as the bifunctional crosslinking reagent a bismaleimide of the structural formula

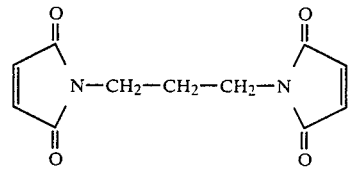

This reagent is prepared according to the method of Goodfriend et alia (Science, 144, 1344–1346 (1964)). As for the remainder the procedure is the same.

The bismaleimides react with sulphydryl groups of proteins and similar molecules by adding onto the double bonds of the maleimide rings.

EXAMPLE 32

Example 30 is modified by using as the bifunctional crosslinking reagent the N-hydroxysuccinimide ester of N-(4)-carboxycyclohexylmethyl)-maleimide.

The reactions occurring in that case are a combination of the reactions involved in example 30 and 31.

EXAMPLE 33

Example 30 is modified by using as the bifunctional crosslinking reagent, the N-hydroxysuccinimide ester of 3(2-pyridyl-dithio)-propionic acid of the formula

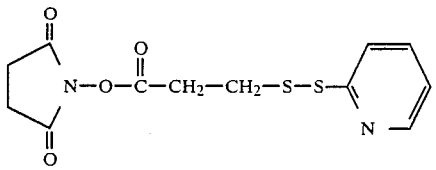

In this example amine groups of protein or the like react with the one end of the cross-linking agent with the elimination of N-hydroxysuccinimide whilst the other end reacts with sulphydryl groups by way of disulphide exchange with the elimination of 2-mercapto-pyridine.

Blocking of unreacted functional groups can once again be carried out with mercapto ethylamine.

It should be noted that examples 14 to 33 are also to be considered as examples which quite generally illustrate the use of various bifunctional linking reagents which can be used in analogous manner for covalently aggregating molecules carrying desired immuno determinants and for linking such molecules to other carrier molecules e.g. albumin or haemocyanin.

EXAMPLE 34

Application of immunogenic determinants to naked bacteria by adsorption

The carboxyl groups of 4-hydroxy-3-methoxybenzoic acid is reacted with hexadecylamine as follows:

504 mg vanilic acid is dissolved in 50 cc methylene chloride and is mixed with 723 mg 1-aminohexadecane dissolved in 100 cc methylene chloride.

303 mg triethylamine and 3 mmol of 1 ethyl-3-(3-dimethylaminopropyl)-carbodiimidehydroxhloride are added to the mixture with magnetic stirring. Agitation is continued for 1 hour whereafter the reaction mixture is washed successively with water, 0.01M HCl, water, 0.01M NaHCO$_3$ and water. The organic phase is dried over calcium chloride which is subsequently filtered off, and the solvent is evaporated off under reduced pressure. The product, N-hexadecyl-4-hydroxy-3-methoxybenzoic acid amide is recrystallised from a mixture of methylene chloride and benzene and dried.

30 mg of dried naked bacteria are reconstituted by being suspended in 6 ml of water and incubated for one hour at 37° C. The supernatant is centrifuged off at 12000 g. The N-hexadecyl-4-hydroxy-3-methoxy benzoic acid amide is dissolved in methanol and added to the reconstituted naked bacteria to form an immunogenic adsorption complex. The product is centrifuged at 12000 g to remove the supernatant and resuspended in 18 ml of PBS for immunisation and IgY recovery as in example 1. A good immune response is attained.

Similar results are obtained with N-(4-hydroxy-3-methoxybenzoyl)-phosphatidylethanolamine produced by reaction in an analogous manner from 504 mg vinylic acid in 50 cc methylenechloride and 2.2 g phosphatidylethanolamine in 100 cc methylenechloride agitated for one hour with 303 mg triethylamine and 3 m mol 1 ethyl-3-(3-dimethylaminopropyl)-carbodiimide hydrochloride. The reaction mixture is again washed with water, dilute hydrochloric acid, water, dilute sodium bicarbonate and water, thereafter the organic phase is dried over calcium chloride and the solvent is evaporated off under reduced pressure. The product is recrystallised from ethanol. The adsorption complex with naked bacteria is formed as above and a good immune response is obtained with hens using this immunogen. In the aforegoing examples 14 to 34 the dosage for immunising the fowls corresponds to about 0.8 mg immunogen per immunisation.

EXAMPLE 35

Rabbit IgG anti-IgY

IgY is bonded to naked bacteria with glutaraldehyde using the procedures described in example 15. This carrier-bound immunoglobulin is then used for the immunisation of rabbits as follows. The suspensions are made up with Freund's incomplete adjuvant, 1 ml of Freund's incomplete adjuvant being added to 1 ml of immunogen suspension and the mixture is shaken up till a stable emulsion is formed. The rabbits are inoculated with this emulsion by the administration of 2×0.5 ml doses injected at two different sites subcutaneously. This is repeated once a week for 8 weeks, whereafter only periodic boosters are given. All injections are accompanied by a simultaneous intromuscular injection of the general antibiotic "Streptopen" ® to guard against infection. After the first week 0.5 ml of 1:5 diluted adrenalin is injected subcutaneously 10 minutes prior to each inoculation as a precaution against anaphylactic shock.

Blood is drawn from the main artery supplying the ear of the rabbit. The blood is allowed to clot at room temperature (20° C.) for 3 to 5 hours and is then centrifuged at 3000×g for 30 minutes. The clear serum obtained is diluted with 2 volumes of borate buffer (0.01 M, pH 8.6) and mixed carefully. Polyethyleneglycol (PEG 6000) is added to a concentration of 15% m/v, followed by centrifugation at 12000×m for 10 minutes. The precipitate pellet is resuspended in the same volume of the borate buffer and the precipitation with PEG 6000 and centrifugation is repeated.

EXAMPLE 36

Concentration of specific antibodies

IgY-anti-T$_3$ recovered from the egg yolk of immunised hens and concentrated in accordance with the procedure described in example 15 is used. The anti-T$_3$ antibodies are further concentrated by the following procedure:

The anti-T$_3$ IgY antibody preparation is dialysed against 0.2M acetic acid for 4 hours to lower the pH to approximately 4. The solution is cooled to 4° C. and the pH is adjusted to 4.6. PEG 6000 is added to a concentration of 8% m/v and the precipitate which forms is centrifuged off at 14000×g. The pH is then raised to 5.0 by the addition of 0.1M sodium hydroxide and the PEG concentration is again adjusted to 8% m/v. The precipitate which forms is centrifuged off and is recovered as a concentrate of IgY molecules with a high T$_3$ binding capacity.

The aforegoing is an example of recovering and concentrating IgY elicited against immunogens of comparatively high molecular weight.

The fraction precipitated at pH 4.6 is enriched in respect of antibodies elicited against immunogens of comparatively low molecular weight. This precipitate may be a product as such.

It is possible to modify this procedure so that the antibodies against high molecular weight immunogens are precipitated first. In that case the pH is first adjusted to about 7.5 and the partial insolubilisation takes place at a PEG 6000 concentration of 8% m/v. Thereafter the pH is lowered to 5.5 and a fraction relatively enriched in antibodies against low molecular weight immunogens is precipitated at that lower pH optionally after increasing the PEG concentration.

It will be appreciated that sharper separations and better purifications are achieved by repeated fractional precipitation with pH control.

EXAMPLE 37

Fractional precipitation of IgG antibodies

The IgG-anti-IgY antibodies prepared in accordance with example 35 are further concentrated by the following procedure: The preparation is dialysed against 0.2 m acetic acid until the pH has been lowered to about 4.5. The solution is cooled to 4° C. and the pH is adjusted to 5.5. PEG 6000 is added to a concentration of 8.5% m/v and the precipitate which forms is centrifuged off at 14000×g. This precipitate is enriched in respect of IgG antibodies against relatively low molecular weight immunogens. Optionally the precipitation is first carried out at a lower pH, e.g. pH 4.5 to recover a first fraction in which antibodies against low molecular weight immunogens are relatively even more concentrated and this is followed by a further precipitation at pH 5.5 which may serve as yet a further product or as an intermediate fraction for redissolving and refractionation.

The pH of the supernatant is then raised to 6.5 by the addition of 0.1M sodium hydroxide and the PEG concentration is adjusted to 10% m/v. The precipitate which forms is centrifuged off and is recovered as a concentrate of specific IgG anti-IgY molecules.

In this case as in Example 36 the sequence of precipitating the antibodies may be reversed by carrying out the first precipitation (antibodies against large immunogens) at relatively high pH (pH 8) and recovering the balance of the antibodies by lowering the pH and/or raising the polymer concentration.

The aforegoing examples involve the use of the most preferred precipitant PEG 6000. However, persons skilled in the art, having due regard to the detailed teachings preceding the examples would have no difficulties in modifying these examples by the analogous substitution of precipitants differing in molecular weight and/or chemical composition.

EXAMPLE 38

Specific antibodies may be made from the immune IgY by the recognised methods of affinity chromatography and by absorbing and elution from immuno-precipitates following the method of G. Hardy and M. H. V. van Regenmortel as published in J. Immunological Methods, Vol. 15, 1977, p305-314.

Specific IgY antibody to human IgG was prepared by affinity chromatography. The yield of the specific IgY was 8%. Immuno specific IgY antibody was prepared by dissociation of the complex of IgY and tobacco mosaic virus (TMV) at pH 2.9 in 0.005M glycine HCl followed by centrifuging to remove the TMV. The total specific IgY isolated represented 18% of the total IgY protein.

Some advantages of the yolk antibody system over the conventional method of production of antisera in mammals are the following:

1. The production of antibodies in the hen and their transfer to the yolks of their eggs continues unabated at a high level of activity once this level has been obtained.

2. The necessity of bleeding and periodic booster injections are obviated, a necessity when conventional laboratory mammals are kept for the purpose of antibody production.

3. The antibody is of the 7 S type and free of IgM. As a result of the method of isolation with polyethylene glycol the antibody is obtained as a single molecular component as shown by analytical ultracentrifugation. The chicken antibody could therefore be advantageous for quantitative determinations by the radical immuno diffusion method. Mixtures of IgM and IgG are known to give erroneous results in this test.

4. As the IgY antibodies are obtained, after the final step in purification, as a semi-solid pellet, it may be dissolved in a small volume of diluent. Hence any desired activity, within limits, may be obtained.

5. The electrophoretic homogeneity of IgY compared to the usual extreme heterogeneity of mammalian IgG could simplify many immunochemical investigations in which purified antibodies are used.

6. Hens are less susceptible to disease than conventional laboratory animals and are housed and fed more economically.

7. Yolk immunoglobulins (IgY) may be extracted from eggs of hens housed on farms specialising in commercial egg production. As hygiene of the housing quarters is of paramount importance as well as the use of hens of the highest production ability, it may be more economical to assign the production of "immune eggs" to such farms rather than to set up an independent poultry unit for the sole purpose of preparing immunological reagents.

8. An additional possibility exists if hens are immunised against snake venoms. The immune IgY may then be used as an alternative to anti-venine produced in horses. This would be a great advantage as a large percentage of people are hyper-sensitive to horse serum proteins. Also, as it requires less antigen to immunise hens than horses, rare anti-venines such as those against the Boomslang and the Bird snake may be produced in sufficient quantity using a relatively small amount of venom.

9. Eggs from immunised hens may be stored at 4° C. for 6 months or longer if desired or required and need only be processed when the antibodies are required. The yolks in a homogenised form and in the presence of sodium azide may be stored at $-20°$ C. virtually indefinitely and the IgY can be extracted when needed.

10. IgY type of antigen against a variety of fowl diseases may, of course also be isolated from the yolks of immunised hens and be used prophylactically in newly hatched or older chicks against diseases which their mothers had not been exposed to yet (examples: New Castle Disease, other virus diseases and a variety of bacterial diseases). This will protect the chicks passively until they can be immunised actively.

The following claims are to be considered as part of the present disclosure.

What is claimed is:

1. A process for producing and isolating IgY antibodies, which comprises the steps of:
   (1) actively immunizing a fowl hen by injecting said hen with an immunogen carrying immunogenic determinants specific to elicit such antibodies, wherein an immunogen having a molecular or particle weight greater than 30,000 daltons, that when injected into a fowl hen induces an immune response;
   (2) continuing to immunize against the determinants by repeatedly injecting said hen with said immunogen over a period of not less than three weeks and at least to that stage of hyperimmunisation which is indicated by a plateau-like levelling-off and persistance of the concentration of antibodies against the determinants in the serum of the fowl;
   (3) after said period, collecting eggs of the immunised hen which now contain said antibodies in the yolk; and
   (4) separating the yolk, separating from the yolk lipid and non-antibody proteinaceous matter and recovering IgY antibodies from the yolk in purified and essentially intact, undamaged form.

2. A process according to claim 1, wherein the immunising is carried out with an immunogen having a molecular or particle weight not less than 100000 daltons.

3. A process according to claim 1, wherein the immunising is carried out with an immunogen having a molecular or particle weight greater than 150000 daltons.

4. A process according to claim 1, wherein the immunogen consists of a hapten attached to a carrier molecule or particle.

5. A process according to claim 4, wherein the carrier molecule or particle to which the hapten is attached is an aggregate of haptens of the same kind.

6. A process according to claim 4, wherein the hapten is covalently bound to the carrier molecule or particle.

7. A process according to claim 6, wherein the carrier molecule or particle is of a different kind than the hapten.

8. A process according to claim 4, wherein the carrier molecules particles carrying the immunogenic determinants are attached to the exterior surface of bacterial particles.

9. A process according to claim 8, wherein the carrier molecules particles are attached to the exterior surface of "naked" bacteria particles by adsorption.

10. A process according to claim 8, wherein the carrier molecules particles are attached to the exterior surface of "naked" bacteria particles by covalent bonding reaction.

11. A process according to claim 4, wherein a hapten or immunogenic determinant having a molecular weight less than 100,000 daltons is covalently bound to a carrier molecule or particle to form an immunogen having a molecular weight more than 150,000 daltons.

12. A process according to claim 4, wherein a hapten or immunogenic determinant having a molecular weight 150,000 daltons or higher is covalently bound to a carrier molecule or particle, thereby causing an enhanced production of antibodies.

13. A process according to claim 1, wherein the immunogenic determinants are foreign to micro organisms associated with natural infective diseases of the fowl.

14. A process according to claim 1, wherein the immunogen is an antibody derived from a different species of animal.

15. A process according to claim 1, wherein cropping of eggs of the immunised hen for the purpose of antibody recovery is continued for a period of months after the immunisation.

16. A process according to claim 1, including a purification or concentration step which comprises forming a two-phase aqueous system, a first phase of the system containing antibodies to be purified or concentrated and a second phase of the system containing dispersed therein a water-soluble linear filamentary, non-charged polymer in a concentration sufficiently high to substantially suppress the solubility or dispersibility of such antibodies and transferring impurities from the first phase to the second phase for removal in the latter.

17. A process according to claim 16, wherein the step involving the two phase aqueous system is preceded by a step of rendering indispersible and separating yolk constituents other than antibodies while maintaining the antibodies in solution or dispersion.

18. A process according to claim 17, wherein the rendering indispersible is carried out using a water-soluble linear filamentary non-charged polymer as a precipitant in a concentration less than that at which substantial precipitation of the antibodies takes place.

19. A process according to claim 16, wherein the first phase contains substantially all the IgY antibodies of the system and the second phase is substantially devoid of antibodies.

20. A process according to claim 16, wherein the step involving the two phase aqueous system comprises introducing into an aqueous dispersion of the antibodies the polymer to a concentration sufficient to selectively substantially suppress the dispersibility of the antibodies and separating purified antibodies thus rendered indispersable from an aqueous phase containing dissolved therein the polymer.

21. A process according to claim 20, wherein the concentration of the polymer corresponds in precipitating power to a concentration of PEG 6000 higher than 11% and lower than 14% by weight per volume of aqueous yolk material.

22. A process according to claim 16, wherein the polymer is selected from the group consisting of polyalkylene glycols and dextran.

23. A process according to claim 22, wherein the molecular weight of the polymer is within the range of 2000 to 30000 daltons.

24. A process according to claim 22, wherein the polymer is polyethyleneglycol with an average molecular weight of from 4000 to 9000 daltons.

25. A process according to claim 1, which further comprises concentrating or purifying a specific IgY fraction selected out of the total of the IgY antibodies recovered from the yolk, comprising:
thoroughly mixing recovered mixed IgY antibodies containing the selected specific IgY antibodies in addition to other IgY antibodies of the total with water, adjusting the pH of the water to a predetermined level in or around the isoelectric pH range of the recovered antibodies and with an amount of water-soluble linear filamentary non-charged polymer sufficiently large to attain only partial suppression of the solubility or dispersibility of the antibodies, followed by the formation and separation of two phases:
A. an aqueous phase wherein a substantial part of the IgY antibodies is dissolved or dispersed,
B. a displaced, non-dissolved or non-dispersed phase containing the remaining part of the IgY antibodies;
one of the phases containing the selected specific IgY antibodies in greater proportion (based on antibody content) than the recovered mixed antibodies; and recovering the antibodies of that phase.

26. A process according to claim 25, wherein the selected specific antibodies are which in greater proportion in the aqueous phase (A) and comprises adjusting the pH of the aqueous phase to a level substantially equal to the isoelectric pH of the selected specific antibodies, precipitating selected specific antibodies at that pH and recovering the precipitated antibodies.

27. A process according to claim 26, wherein the concentration of the polymer is increased at that pH to promote the precipitation of the selected specific antibodies.

28. A process according to claim 1, wherein the antibodies are separated and recovered by a separation process comprising the steps of
(a) rendering the lipid content and the caseinous protein of the egg yolk water-indispersible by mixing the yolk with water and a water-soluble linear filamentary noncharged polymer precipitant in a concentration sufficient to substantially suppress the dispersibility of lipids and caseinous protein without substantially suppressing the dispersibility of IgY antibodies;
(b) separating egg yolk substances thus rendered indispersible, including the lipid content, from an aqeuous phase which still contains the antibodies dispersed therein; and
(c) recovering the antibodies from said aqueous phase.

29. A process according to claim 28, wherein step (c) comprises increasing the concentration of the water-soluble linear filamentary non-charged polymer precipitant to a concentration sufficient to selectively substantially suppress the dispersibility of the antibodies, and separating purified substantially homogeneous antibodies thus rendered indispersible from an aqueous phase containing the precipitant.

30. A process according to claim 1, wherein the immunogen used for actively immunising the fowl carries immunogenic determinants adapted to specifically elicit IgY antibodies which can bind antigens which give rise to a pathological condition in a mammal.

31. A process according to claim 30, wherein the immunogen carries immunogenic determinants of pathogenic micro-organisms responsible for a disease; whereby the resultant IgY can be injected to protect the mammal against the micro-organism.

32. A process according to claim 30, wherein the immunogen carries immunogenic determinants of a toxin or venom.

33. A process according to claim 25, wherein said pH is between about 4 and 6.

34. A process according to claim 25, which comprises selectively insolubilising first antibodies of the mixture which have been elicited against immunogens of relatively low molecular or particle weight whilst selectively leaving in aqueous solution or dispersion second antibodies of the mixture being antibodies against immunogens of higher molecular or particle weight than the immunogens of relatively low molecular weight by adjusting the pH to a level below the isoelectric pH for the second antibodies and adjusting the amount of the polymer to attain the partial suppression at that level.

35. A process according to claim 25, which comprises selectively insolubilising second antibodies of the mixture which have been elicited aganst immunogens of relatively high molecular or particle weight whilst selectively leaving in aqueous solution or dispersion first antibodies of the mixture being antibodies against immunogens of lower molecular or particle weight than the immunogens of relatively high molecular weight by adjusting the pH to a level above the isoelectric pH for the first antibodies and adjusting the amount of the polymer to attain the partial suppression at that level.

36. An antibody preparation consisting essentially of IgY antibodies produced by the process of claim 1.

37. An antibody preparation according to claim 36, wherein the IgY has been elicited against antibodies from a different animal.

38. An antibody preparation according to claim 36, wherein the IgY has been elicited against haptens or immunogenic determinants which as such have a molecular or particle weight less than 100000 daltons.

39. An antibody preparation according to claim 38, wherein the IgY has been elicited against haptens or immunogenic determinants which as such have a molecular or particle weight less than 30000 daltons.

40. An antibody preparation according to claim 38, wherein the IgY has been elicited against alpha-fetoprotein.

41. An antibody preparation according to claim 38, wherein the IgY has been elicited against albumin.

42. An antibody preparation according to claim 36, wherein the IgY has been elicited in response to an immunogen comprising the immunogenic determinants, grafted onto a carrier molecule or particle, the total molecular or particle weight of the immunogen being not less than 30000 daltons.

43. An antibody preparation according to claim 42, wherein the IgY has been elicited in response to such immunogen having a total or particle weight of not less than 100000 daltons.

44. An antibody preparation according to claim 41, wherein the IgY has been elicited in response to such immunogen comprising the immunogenic determinant covalently bonded to a carrier molecule or particle.

45. An antibody preparation according to claim 44, wherein the IgY has been elicited in response to such immunogen comprising the immunogenic determinant covalently bonded to a protein molecule foreign to the determinant.

46. An antibody preparation according to claim 42, wherein the IgY has been elicited in response to such immunogen comprising the immunogenic determinant attached to the exterior of a bacterial particle as carrier.

47. An antibody preparation according to claim 46, wherein the IgY has been elicited in response to such immunogen comprising the immunogenic determinant bound to the exterior of a naked bacteria particle as carrier.

48. An antibody preparation according to claim 47, wherein the IGY has been elicited in response to such immunogen comprising the immunogenic determinant adsorptively bound to the exterior of a naked bacterium particle as carrier.

49. An antibody preparation according to claim 47, wherein the IgY has been elicited in response to such immunogen comprising the immunogenic determinant covalently bonded to the exterior of a naked bacterium particle.

50. An antibody preparation according to claim 36, useful for pathological or forensic diagnosis or testing, wherein said IgY has been elicited to be specific against a hapten or antigen the presence or quantity of which in a pathological or forensic sample is diagnostically or forensically significant.

51. An antibody preparation according to claim 36, wherein the IgY has been elicited in response to immunogenic determinants specific to a toxin, venom or a micro-organism which is non-pathogenic to the hen but which is pathogenic to another animal.

52. An antibody preparation according to claim 68, capable of use in an immuno-binding test, wherein said IgY antibodies recovered from egg yolk are elicited in the egg yolk by immune response of said fowl hen against an immunogen comprising antibodies of a mammalic species.

53. In a process or passively immunising a mammal, the term including humans, against disease, poisoning or another pathological condition against or from which the immunisation is to afford protection or relief, which comprises injecting into the mammal antibodies specific against antigens which give rise to said condition, in a dosage adapted to produce a passive immunity against the condition, the improvement wherein said specific antibodies are
IgY antibodies produced by:
(1) actively immunizing a fowl hen by injecting said hen with an immunogen carrying immunogenic determinants specific to elicit such antibodies, wherein the immunogen is selected with such molecular or particle weight, being not less than 30,000 daltons, and carries the determinants in such number and so exposed on the immunogen that an immune response is elicited in the fowl;
(2) continuing to immunize against the determinants by repeatedly injecting said hen with said immunogen over a period of not less than three weeks and at least to that stage of hyperimmunisation which is indicated by a plateau-like levelling-off and persistance of the concentration of antibodies against the determinants in the serum of the fowl;

(3) after said period, collecting eggs of the immunised hen which now contain said antibodies in the yolk; and (4) separating the yolk, separating from the yolk lipid and non-antibody proteinaceous matter and recovering IgY antibodies from the yolk in purified and essentially intact, undamaged form.

54. A process according to claim 53, wherein the antibodies are recovered and purified by a separation, wherein the antibodies are separated from contaminants by selective precipitation using a water-soluble, linear, filamentary, non-charged polymer as a precipitant.

55. In an immuno-assay kit or an ELISA kit, comprising an antibody preparation having a desired specificity for an antigen or hapten, together with ancillary reagents, the improvement wherein the antibody is prepared by:

(1) actively immunizing a fowl hen by injecting said hen with an immunogen carrying immunogenic determinants specific to elicit such antibodies, wherein the immunogen is selected with such molecular or particle weight, being not less than 30,000 daltons, and carries the determinants in such number and so exposed on the immunogen that an immune response is elicited in the fowl;

(2) continuing to immunize against the determinants by repeatedly injecting said hen with said immunogen over a period of not less than three weeks and at least to that stage of hyperimmunisation which is indicated by a plateau-like levelling-off and persistance of the concentration of antibodies against the determinants in the serum of the fowl;

(3) after said period, collecting eggs of the immunised hen which now contain said antibodies in the yolk;

(4) separating the yolk, separating from the yolk lipid and non-antibody proteinaceous matter and recovering IgY antibodies from the yolk in purified and essentially intact, undamaged form;

said antibody preparation being useful for pathological or forensic diagnosis or testing, wherein said IgY has been elicited to be specific against a hapten or antigen the presence or quality of which in a pathological or forensic sample is diagnostically or forensically significant.

56. In a process for producing mammalian antibodies wherein a mammal is actively immunized against an antigen, and antibodies against said antigen are recovered from said mammal, the improvement wherein said antigen is an antibody preparation prepared by:

(1) actively immunizing a fowl hen by injecting said hen with an immunogen carrying immunogenic determinants specific to elicit such antibodies, wherein the immunogen is selected with such molecular or particle weight, being not less than 30,000 daltons, and carries the determinants in such number and so exposed on the immunogen that an immune response is elicited in the fowl;

(2) continuing to immunize against the determinants by repeatedly injecting said hen with said immunogen over a period of not less than three weeks and at least to that stage of hyperimmunisation which is indicated by a plateau-like levelling-off and persistance of the concentration of antibodies against the determinants in the serum of the fowl;

(3) after said period, collecting eggs of the immunised hen which now contain said antibodies in the yolk; and (4) separating the yolk, separating from the yolk lipid and non-antibody proteinaceous matter and recovering IgY antibodies from the yolk in purified and essentially intact, undamaged form.

57. In a pathological, forensic or micro-analytical immuno-binding test for a substance, wherein an analyte is contacted with an antibody preparation specific to said substance, and an antigen-antibody interaction is detected, the improvement wherein said antibody preparation is an antibody preparation prepared by:

(1) actively immunizing a fowl hen by injecting said hen with an immunogen carrying immunogenic determinants specific to elicit such antibodies, wherein the immunogen is selected with such molecular or particle weight, being not less than 30,000 daltons, and carries the determinants in such number and so exposed on the immunogen that an immune response is elicited in the fowl;

(2) continuing to immunize against the determinants by repeatedly injecting said hen with said immunogen over a period of not less than three weeks and at least to that stage of hyperimmunisation which is indicated by a plateau-like levelling-off and persistance of the concentration of antibodies against the determinants in the serum of the fowl;

(3) after said period, collecting eggs of the immunised hen which now contain said antibodies in the yolk; and (4) separating the yolk, separating from the yolk lipid and non-antibody proteinaceous matter and recovering IgY antibodies from the yolk in purified and essentially intact, undamaged form.

58. A process according to claim 57, wherein said immunobinding test is a quantitative immuno assay.

59. An antibody preparation according to claim 51, which is specific against a toxin or venom.

* * * * *